(12) United States Patent
Warshawsky et al.

(10) Patent No.: US 6,352,976 B1
(45) Date of Patent: Mar. 5, 2002

(54) SELECTIVE INHIBITORS OF MMP-12

(75) Inventors: Alan M. Warshawsky, Carmel, IN (US); Michael J. Janusz, Oregonia, OH (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/464,908

(22) Filed: Dec. 17, 1999

Related U.S. Application Data

(60) Provisional application No. 60/155,223, filed on Dec. 31, 1998, now abandoned.

(51) Int. Cl.$^7$ .................. A61K 38/05; A61K 38/06; C07K 5/06; C07K 5/08
(52) U.S. Cl. .................. 514/18; 514/19; 514/20; 530/331; 562/426
(58) Field of Search .................. 514/18, 19, 20; 530/331; 562/426

(56) References Cited

U.S. PATENT DOCUMENTS

| | | | |
|---|---|---|---|
| 4,613,587 A | 9/1986 | Kessler et al. .................. | 514/19 |
| 5,508,266 A | 4/1996 | Fink .................. | 514/19 |
| 5,591,891 A | 1/1997 | Fournie-Zaluski et al. .. | 567/426 |
| 5,760,241 A | 6/1998 | Santangelo et al. .......... | 548/204 |
| 5,866,604 A | 2/1999 | Pellacini .................. | 514/506 |

FOREIGN PATENT DOCUMENTS

| | | |
|---|---|---|
| EP | 0524553 | 1/1993 |
| WO | 9302099 | 2/1993 |
| WO | 9417036 | 8/1994 |
| WO | 9535315 | 12/1995 |
| WO | 9622998 | 8/1996 |
| WO | 9738007 | 10/1997 |
| WO | 9804287 | 2/1998 |
| WO | 9935124 | 7/1999 |

OTHER PUBLICATIONS

Knight et al. A novel coumarin–labelled peptide for sensitive . . . FEBS Lett. vol. 296, No. 3, pp. 263–266, Jan. 1992.*
Beaumont et al. The Role of Histidine 231 . . . J. Biol. Chem. vol. 270, No. 28, pp. 16803–16808, Jul. 14, 1995.*
Coric et al., *J. Med. Chem.* 39, 1210–1219 (1996).
Fink et al., *J. Med. Chem.* 38, 5023–5030 (1995).
Gaucher et al., *Biochemistry* 38, pp. 12569–12576 (1999).

* cited by examiner

*Primary Examiner*—Jeffrey E. Russel
(74) *Attorney, Agent, or Firm*—Julie Anne Knight

(57) ABSTRACT

The present invention provides novel mercaptoacetylamido dipeptide carboxylic acids of the formula formula (1)

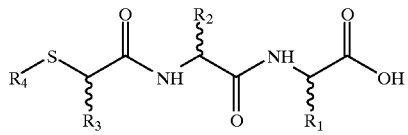

which are MMP inhibitors useful for the treatment of smoking-induced emphysema.

21 Claims, No Drawings

SEQUENCE LISTING

<160> NUMBER OF SEQ ID NOS: 1

<210> SEQ ID NO 1
<211> LENGTH: 7
<212> TYPE: PRT
<213> ORGANISM: Artificial sequence

```
<220> FEATURE:
<223> OTHER INFORMATION: Synthetic Construct
<221> NAME/KEY: MISC_FEATURE
<222> LOCATION: (5)..(5)
<223> OTHER INFORMATION: Xaa at position 5 is N-3-(2,4-dinitrophenyl)-
      L-2,3-diaminopropionyl

<400> SEQUENCE: 1

Pro Leu Gly Leu Xaa Ala Arg
1               5
```

SELECTIVE INHIBITORS OF MMP-12

This application claims the benefit of U.S. Provisional Application No. 60/155,223, filed Dec. 31, 1998.

BACKGROUND OF THE INVENTION

The discovery of different families of matrix metalloproteinases (MMPs), their relationships, and their individual characteristics have been categorized in several reports. Emonard, H. et al., *Cell Molec. Biol.* 36, 131–153 (1990); Birkedal-Hansen, H., *J. Oral Pathol.* 17, 445–451 (1988); Matrisian, L. M., *Trends Genet.* 6, 121–125 (1990); Murphy, G. J. P. et al., *FEBS Lett.* 289, 4–7 (1991); Matrisian, L. M., Bioessays 14, 455–463 (1992). Beckett, R. P. et al., *DDT* 1, 16–26 (1996).

The MMPs are a family of zinc containing endopeptidases which are capable of cleaving large biomolecules, such as the extracellular matrix they are generally secreted in latent form and require activation by proteolytic enzymes, and they are regulated by specific endogenous inhibitors. Three broad groups of MMPs have been delineated: the collagenases which have triple helical interstitial collagen as a substrate, the gelatinases which are proteinases of denatured collagen and Type IV collagen, and the stromelysins which were originally characterized as proteoglycanases but have now been identified to have a broader proteolytic spectrum. Examples of specific MMPs, include, in the collagenases, fibroblast collagenase (MMP-1); in the gelatinases 72 kDa gelatinase (gelatinase A; MMP-2); and in stromelysins include stromelysin 1 (MMP-3). Other MMPs do not fit neatly into the above groups, for example macrophage metalloelastase (MMP-12). Beckett, R. P. et al., *DDT* 1, 16–26 (1996).

The characterizing feature of diseases involving the MMP enzymes appears to be a stoichiometric imbalance between active enzymes and endogenous inhibitors, leading to excessive tissue disruption, and often degradation. McCachren, S. S., *Arthritis Rheum.* 34, inflammatory disorders, such as emphysema; cardiovascular disorders, such as atherosclerosis; corneal ulceration; dental diseases such as gingivitis and periodontal disease; and neurological disorders such as multiple sclerosis. Chirivi, R. G. S. et al., *Int. J. Cancer*, 58, 460–464 (1994); Zucker, S., Cancer Research, 53, 140–146 (1993). In addition, a recent study indicates that MMP-12 is required for the development of smoking-induced emphysema in mice. Science, 277, 2002 (1997).

Apart from the role of these potentially very destructive enzymes in pathology, the MMPs play an essential role in cell regrowth and turnover in healthy tissue. Broad spectrum inhibition of the MMPs in the clinical setting results in musculoskeletal stiffness and pain. H. S. Rasmussen and P. P. McCann, *Pharmacol. Ther.*, 75, 69–75 (1997). This side effect and others associated with broad spectrum inhibition may be enhanced in chronic administration. Thus, it would be advantageous to provide selective MMP inhibitors.

Surprisingly, we have found that the mercaptoacetylamido dipeptide carboxylic acids of the present application are selective inhibitors of MMP-12 compared to their N-methylamide derivatives. Specifically, while known broad spectrum inhibitors having an amide terminus have inhibiting activities with respect to MMP-1, MMP-2, and MMP-3 (PCT Application No. WO 96/11209, published Apr. 18, 1996) the compounds of the present invention are selective for MMP-12 over MMP-1, MMP-2, and MMP-3 compared to their N-methylamide derivatives. These selective inhibitors are useful for the treatment of smoking-induced emphysema. Because they are selective, the compounds of the present application are expected to be useful for long term therapy with less of the complications related to broad spectrum inhibition.

SUMMARY OF THE INVENTION

The present invention provides novel mercaptoacetylamido dipeptide carboxylic acids of the formula

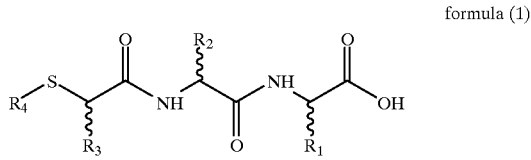

formula (1)

wherein $R_1$ is selected from the group consisting of hydrogen, $C_1$–$C_6$ alkyl, —$(CH_2)_a$—$CO_2R_5$, —$(CH_2)_a$—$C(O)NH_2$, —$(CH_2)_4NH_2$, —$(CH_2)_3$—NH—$C(NH)NH_2$, —$(CH_2)_2$—$S(O)_b$—$CH_3$, —$CH_2$—OH, —$CH(OH)CH_3$, —$CH_2$—SH, —$(CH2)_d$—$Ar_1$, and —$CH_2$—$Ar_2$;

wherein a is 1 or 2;

b is 0, 1, or 2;

d is an integer from 0 to 4;

$R_5$ is selected from the group consisting of hydrogen, $C_1$–$C_4$ alkyl, and benzyl;

$Ar_1$ is a radical selected from the group consisting of

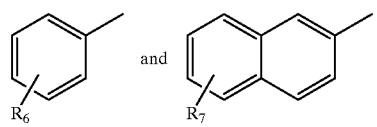

wherein $R_6$ is from 1 to 2 substituents independently selected from the group consisting of hydrogen, halogen, $C_1$–$C_4$ alkyl, hydroxy, and $C_1$–$C_4$ alkoxy;

$R_7$ is selected from the group consisting of hydrogen, halogen, $C_1$–$C_4$ alkyl, and $C_1$–$C_4$ alkoxy;

$Ar_2$ is a radical selected from the group consisting of

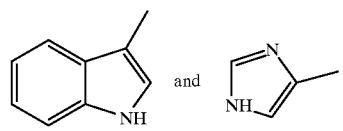

$R_2$ is selected from the group consisting of $C_1$–$C_6$ alkyl, —$(CH_2)_e$—$CO_2R_{5'}$, —$(CH_2)_e$—$C(O)NH_2$, —$(CH_2)_4NH_2$, —$(CH_2)_3$—NH—$C(NH)NH_2$, —$(CH_2)_2$—$S(O)_f$—$CH_3$, —$CH_2$—OH, —$CH(OH)CH_3$, —$CH_2$—SH, —$(CH_2)_g$—$Ar_{1'}$, and —$(CH_2)$—$Ar_{2'}$;

wherein e is 1 or 2;

f is 0, 1, or 2;

g is an integer from 1 to 4;

$R_5$ is selected from the group consisting of hydrogen, $C_1$–$C_4$ alkyl, and benzyl;

$Ar_{1'}$ is a radical selected from the group consisting of

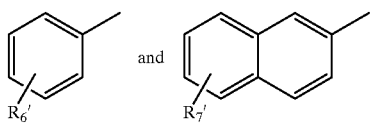

wherein $R_6$ is from 1 to 2 substituents independently selected from the group consisting of hydrogen, halogen, $C_1$–$C_4$ alkyl, hydroxy, and $C_1$–$C_4$ alkoxy;

$R_7$ is selected from the group consisting of hydrogen, halogen, $C_1$–$C_4$ alkyl, and $C_1$–$C_4$ alkoxy;

$Ar_{2'}$ is a radical selected from the group consisting of

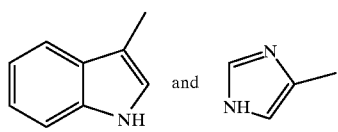

$R_3$ is selected from the group consisting of $C_1$–$C_6$ alkyl, —$(CH_2)_m$—W, —$(CH_2)_p$—$Ar_3$, —$(CH_2)_k$—$CO_2R_9$, —$(CH_2)_m$—$SO_2NR_{8'}$—$Y_1$, —$(CH_2)_m$—Z—Q wherein m is an integer from 2 to 8;

is an integer from 0–10;

k is an integer from 1 to 9;

W is phthalimido;

$Ar_3$ is selected from the group consisting of

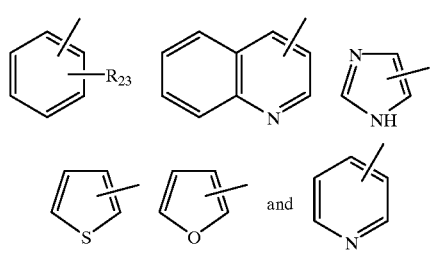

wherein $R_{23}$ is from 1 to 2 substituents independently selected from the group consisting of hydrogen, halogen, $C_1$–$C_4$ alkyl, and $C_1$–$C_4$ alkoxy;

$R_{8'}$ is hydrogen or $C_1$–$C_6$ alkyl;

$R_9$ is hydrogen or $C_1$–$C_6$ alkyl;

$Y_1$ is selected from the group consisting of hydrogen, —$(CH_2)_j$—$Ar_4$, —$N(R_{24})_2$, or $Y_1$ and $R_{8'}$ are taken together with the nitrogen to which they are attached to form N-morpholino, N-piperidino, N-pyrrolidino, or N-isoindolyl;

wherein j is 0 or 1;

$R_{24}$ is hydrogen or $C_1$–$C_6$ alkyl;

$Ar_4$ is

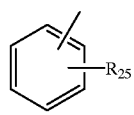

wherein $R_{25}$ is from 1 to 3 substituents independently selected from the group consisting of hydrogen, halogen, $C_1$–$C_4$ alkyl, and $C_1$–$C_4$ alkoxy;

Z is selected from the group consisting of —O—, —$NR_8$—, —C(O)$NR_8$—, —$NR_8$C(O)—, —$NR_8$C(O)NH—, —$NR_8$C(O)O—, and —OC(O)NH—;

wherein $R_8$ is hydrogen or $C_1$–$C_6$ alkyl;

Q is selected from the group consisting of hydrogen, —$(CH_2)_n$—$Y_2$, and —$(CH_2)_x Y_3$;

wherein n is an integer from 0 to 4;

$Y_2$ is selected from the group consisting of hydrogen, —$(CH_2)_h$—$Ar_5$ and —$(CH_2)_t$—C(O)$OR_{27}$ wherein $Ar_5$ is selected from the group consisting of

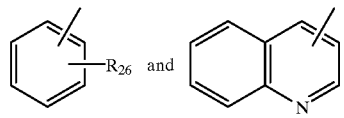

wherein $R_{26}$ is from 1 to 3 substituents independently selected from the group consisting of hydrogen, halogen, $C_1$–$C_4$ alkyl, and $C_1$–$C_4$ alkoxy;

h is an integer from 0 to 6;

t is an integer from 1 to 6;

$R_{27}$ is hydrogen or $C_1$–$C_6$ alkyl;

x is an integer from 2 to 4;

$Y_3$ is selected from the group consisting of —$N(R_{28})_2$, N-morpholino, N-piperidino, N-pyrrolidino, and N-isoindolyl;

wherein $R_{28}$ is hydrogen or $C_1$–$C_6$ alkyl;

$R_4$ is selected from the group consisting of hydrogen, —C(O)$R_{10}$, —C(O)—$(CH_2)_q$—X and —S—G wherein $R_{10}$ is selected from the group consisting of hydrogen, $C_1$–$C_4$ alkyl, phenyl, and benzyl;

q is 0, 1, or 2;

X is selected from the group consisting of

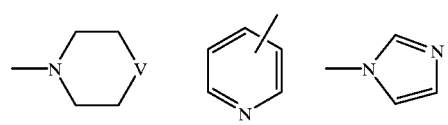

-continued

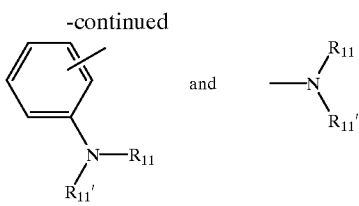

wherein
V is selected from the group consisting of a bond, —CH$_2$—, —O—, —S(O)$_r$—, —NR$_{21}$—, and —NC(O)R$_{22}$—;
wherein
r is 0, 1, or 2;
R$_2$ is selected from the group consisting of hydrogen, C$_1$-C$_4$ alkyl, and benzyl;
R$_{22}$ is selected from the group consisting of hydrogen, —CF$_3$, C$_1$-C$_{10}$ alkyl, phenyl, and benzyl;
R$_{11}$ is selected from the group consisting of hydrogen, C$_1$-C$_4$ alkyl, and benzyl;
R$_{11'}$ is selected from the group consisting of hydrogen, C$_1$-C$_4$ alkyl, and benzyl;
G is selected from the group consisting of

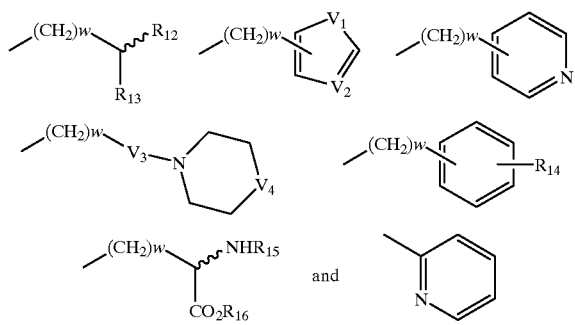

wherein
w is an integer from 1 to 3;
R$_{12}$ is selected from the group consisting of hydrogen, C$_1$-C$_6$ alkyl, —CH$_2$CH$_2$S(O)$_u$—CH$_3$, and benzyl; wherein u is 0,1, or 2;
R$_{13}$ is selected from the group consisting of hydrogen, hydroxy, amino, C$_1$-C$_6$ alkyl, N-methylamino, N,N-dimethylamino, —CO$_2$R$_{17}$, and —OC(O)R$_8$;
wherein
R$_{17}$ is hydrogen, —CH$_2$O—C(O)C(CH$_3$)$_3$, C$_1$-C$_4$ alkyl, benzyl, or diphenylmethyl;
R$_{18}$ is hydrogen, C$_1$-C$_6$ alkyl or phenyl;
R$_{14}$ is 1 or 2 substituents independently selected from the group consisting of hydrogen, C$_1$-C$_4$ alkyl, C$_1$-C$_4$ alkoxy, or halogen;
V$_1$ is selected from the group consisting of —O—, —S—, and —NH—;
V$_2$ is selected from the group consisting of —N— and —CH—;
V$_3$ is selected from the group consisting of a bond and —C(O)—;
V$_4$ is selected from the group consisting of —O—, —S—, —NR$_{19}$—, and —NC(O)R$_{20}$;
wherein
R$_{19}$ is hydrogen, C$_1$-C$_4$ alkyl, or benzyl;
R$_{20}$ is hydrogen, —CF$_3$, C$_1$-C$_{10}$ alkyl, or benzyl;
R$_{15}$ is selected from the group consisting of hydrogen, C$_1$-C$_6$ alkyl and benzyl;

R$_{16}$ is selected from the group consisting of hydrogen and C$_1$-C$_4$ alkyl; and stereoisomers, pharmaceutically acceptable salt, and hydrate thereof.

The present invention further provides a method of treating smoking-induced emphysema in a patient in need thereof comprising administering to the patient an effective amount of a compound of formula (1).

In addition, the present invention provides pharmaceutical compositions comprising an assayable amount of a compound of formula (1) in admixture or otherwise in association with an inert carrier. The present invention also provides a pharmaceutical composition comprising an effective amount of a compound of formula (1) in admixture or otherwise in association with one or more pharmaceutically acceptable carriers or excipients.

As is appreciated by one of ordinary skill in the art the mercaptoacetylamido dipeptide carboxylic acids of formula (1) exist as stereoisomers. Specifically, it is recognized that they exist as stereoisomers at the point of attachment of the substituents R$_1$, R$_2$, R$_3$, and R$_4$, R$_{12}$, and —NHR$_{15}$. Where indicated the compounds follow either the (+)- and (−)- designation for optical rotation, the (D)- and (L)- designation of relative stereochemistry, or the Cahn-Ingold-Prelog designation of (R)- and (S)- for the stereochemistry of compounds represented by formula (1) and intermediates thereof. Any reference in this application to one of the compounds of the formula (1) is meant to encompass either specific stereoisomers or a mixture of stereoisomers.

The specific stereoisomers can be prepared by stereospecific synthesis using enantiomerically pure or enantiomerically enriched starting materials which are well known in the art. The specific stereoisomers of amino acid starting materials can be prepared by stereospecific synthesis as is well known in the art or analogously known in the art, such as D. A. Evans, et al. *J. Am. Chem. Soc.*, 112, 4011–4030 (1990); S. Ikegami et al. *Tetrahedron*, 44, 5333–5342 (1988); W. Oppolzer et al. *Tet. Lets.* 30, 6009–6010 (1989); *Synthesis of Optically Active α-Amino-Acids*, R. M. Williams (Pergamon Press, Oxford 1989); M. J. O'Donnell ed.: *α-Amino-Acid Synthesis*, Tetrahedron Symposia in print, No. 33, *Tetrahedron* 44, No. 17 (1988); U. Schöllkopf, *Pure Appl. Chem.* 55, 1799 (1983); U. Hengartner et al. *J. Org. Chem.*, 44, 3748–3752 (1979); M. J. O'Donnell et al. *Tet. Lets.*, 2641–2644 (1978); M. J. O'Donnell et al. *Tet. Lets.* 23, 4255–4258 (1982); M. J. O'Donnell et al. *J. Am. Chem. Soc.*, 110, 8520–8525 (1988).

The specific stereoisomers of either starting materials or products can be resolved and recovered by techniques known in the art, such as chromatography on chiral stationary phases, enzymatic resolution, or fractional recrystallization of addition salts formed by reagents used for that purpose. Useful methods of resolving and recovering specific stereoisomers are known in the art and are described in *Stereochemistry of Organic Compounds*, E. L. Eliel and S. H. Wilen, Wiley (1994) and *Enantiomers, Racemates, and Resolutions*, J. Jacques, A. Collet, and S. H. Wilen, Wiley (1981).

As used in this application:
a) the term "halogen" refers to a fluorine atom, chlorine atom, bromine atom, or iodine atom;
b) the term "C$_1$-C$_6$ alkyl" refers to a branched or straight chained alkyl radical containing from 1 to 6 carbon atoms, such as methyl, ethyl, n-propyl, isopropyl, n-butyl, isobutyl, t-butyl, pentyl, hexyl, etc.;
c) the term "C$_1$-C$_4$ alkyl" refers to a saturated straight or branched chain alkyl group containing from 1–4 carbon atoms and includes methyl, ethyl, propyl, isopropyl, n-butyl, s-butyl, isobutyl, and t-butyl;

d) the term "$C_1$–$C_4$ alkoxy" refers to a straight or branched alkoxy group containing from 1 to 4 carbon atoms, such as methoxy, ethoxy, n-propoxy, isopropoxy, n-butoxy, isobutoxy, t-butoxy, etc.;

e) the designation "∧∧∧" refers to a bond for which the stereochemistry is not designated;

f) the designation "◀━" refers to a bond that protrudes forward out of the plane of the page.

g) the designation "⋯⋯⫤" refers to a bond that protrudes backward out of the plane of the page.

h) as used in the examples and preparations, the following terms have the meanings indicated: "g" refers to grams, "mg" refers to milligrams, "μg" refers to micrograms, "mol" refers to moles, "mmol" refers to millimoles, "nmole" refers to nanomoles, "L" refers to liters, "mL" or "ml" refers to milliliters, "μL" refers to microliters, "° C." refers to degrees Celsius, "$R_f$" refers to retention factor, "mp" refers to melting point, "dec" refers to decomposition, "bp" refers to boiling point, "mm of Hg" refers to pressure in millimeters of mercury, "cm" refers to centimeters, "nm" refers to nanometers, "brine" refers to a saturated aqueous sodium chloride solution, "M" refers to molar, "mM" refers to millimolar, "μM" refers to micromolar, "nM" refers to nanomolar, "HPLC" refers to high performance liquid chromatography, "HRMS" refers to high resolution mass spectrum, "DMF" refers to dimethylformamide, "μCi" refers to microcuries, "i.p." refers to intraperitoneally, "i.v." refers to intravenously, and "DPM" refers to disintegrations per minute;

i) for substituent Z, the designations —C(O)NR$_8$—, —NR$_8$C(O)—, —NR$_8$C(O)NH—, —NR$_8$C(O)O—, —OC(O)NH—, and —SO$_2$NR$_8$— refer to the functionalities represented, respectively, by the following formulae showing the attachment of the group (Q):

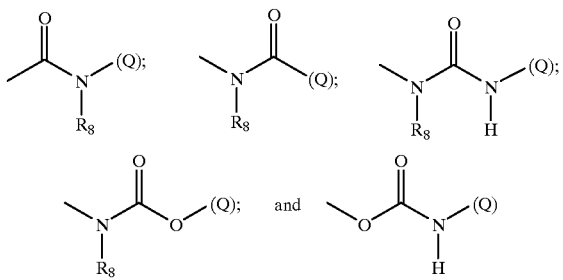

these designations are referred to hereinafter as amido, amide, urea, N-carbamoyl, and O-carbamoyl, respectively;

j) the term "pharmaceutically acceptable salts" thereof refers to either an acid addition salt or a basic addition salt.

The expression "pharmaceutically acceptable acid addition salts" is intended to apply to any non-toxic organic or inorganic acid addition salt of the base compounds represented by formula (1) or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1) or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

As with any group of structurally related compounds which possess a particular utility, certain groups and configurations of substituents are preferred for the compounds of formula (1). Preferred embodiments are given below:

The compounds in which $R_1$ is —(CH$_2$)$_d$—Ar$_1$ are preferred;

The compounds in which $R_1$ is —(CH$_2$)$_d$—Ar$_1$ and Ar$_1$ is the radical

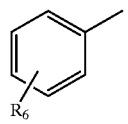

and d is 1 and 2 are more preferred;

Compounds in which $R_2$ is selected from the group consisting of $C_1$–$C_6$ alkyl, —(CH$_2$)$_4$NH$_2$, —(CH$_2$)$_2$—S(O)$_f$—CH$_3$, and —(CH$_2$)$_g$—Ar$_1$, are preferred;

Compounds in which $R_3$ is selected from the group consisting of $C_1$–$C_6$ alkyl, and —(CH$_2$)$_m$—W are preferred;

Compounds in which $R_3$ is 2-propyl are more preferred;

Compounds in which $R_4$ is hydrogen, —C(O)R$_{10}$ and —S—G are preferred;

Compounds in which $R_4$ is —C(O)R$_{10}$ and $R_{10}$ is $C_1$–$C_4$ alkyl more preferred;

Compounds in which $R_4$ is —S—G and G is a radical selected from the group

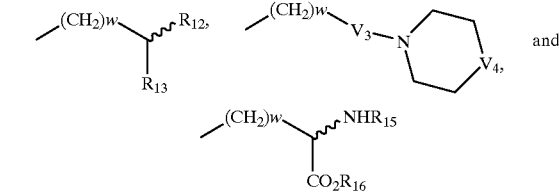

are more preferred.

Examples of compounds encompassed by the present invention include the following. It is understood that the examples encompass all of the isomers of the compound and mixtures thereof. This list is meant to be representative only and is not intended to limit the scope of the invention in any way:

2-mercapto-pentanoyl-homo-phenylalanyl-phenylalanine;
2-mercapto-pentanoyl-leucyl-phenylalanine;
2-mercapto-pentanoyl-methionyl-phenylalanine;
2-mercapto-pentanoyl-lysyl-phenylalanine;
2-mercapto-pentanoyl-t-leucyl-phenylalanine;
2-mercapto-3-methylbutyroyl-homo-phenylalanyl-phenylalanine;
2-mercapto-3-methylbutyroyl-leucyl-phenylalanine;

2-mercapto-3-methylbutyroyl-methionyl-phenylalanine;
2-mercapto-3-methylbutyroyl-lysyl-phenylalanine;
2-mercapto-3-methylbutyroyl-t-leucyl-phenylalanine;
2-thioacetyl-pentanoyl-homo-phenylalanyl-phenylalanine;
2-thioacetyl-pentanoyl-leucyl-phenylalanine;
2-thioacetyl-pentanoyl-methionyl-phenylalanine;
2-thioacetyl-pentanoyl-lysyl-phenylalanine;
2-thioacetyl-pentanoyl-t-leucyl-phenylalanine;
2-thioacetyl-3-methylbutyroyl-homo-phenylalanyl-phenylalanine;
2-thioacetyl-3-methylbutyroyl-leucyl-phenylalanine;
2-thioacetyl-3-methylbutyroyl-methionyl-phenylalanine;
2-thioacetyl-3-methylbutyroyl-lysyl-phenylalanine; and
2-thioacetyl-3-methylbutyroyl-leucyl-phenylalanine.

The compounds of formula (1) can be prepared by a variety of procedures readily known to those skilled in the art. Such procedures include, peptide coupling, such as solid phase sequential procedures and solution phase sequential procedures using suitable amino acids and substituted acids and displacement, modification, and functionalization procedures, as required, utilizing suitable protecting groups and deprotection procedures.

As used herein the term "amino acid" refers to naturally occurring amino acids as well as non-naturally occurring amino acids having substituents encompassed by $R_1$ and $R_2$ as described above. The naturally occurring amino acids included are glycine, alanine, valine, leucine, isoleucine, serine, methionine, threonine, phenylalanine, tyrosine, tryptophan, cysteine, histidine, aspartic acid, asparagine, glutamic acid, glutamine, arginine, ornithine, and lysine. Non-naturally occurring amino acids within the term "amino acid," include without limitation, the D-isomers of the naturally occurring amino acids, norleucine, norvaline, alloisoleucine, t-butylglycine, methionine sulfoxide, and methionine sulfone. Other non-naturally occurring amino acids within the term "amino acid," include without limitation phenylalanines substituted by $R_6$ and $R_{6'}$ as described above; phenylglycines, homophenylalanines, 3-phenylpropylglycines, 4-phenylbutylglycines; including those substituted by $R_6$ and $R_{6'}$ as described above; and 2-naphthylalanines, including those substituted by $R_7$ and $R_{7'}$ as described above.

Solid phase sequential procedures can be performed using established methods, including automated methods such as by use of an automated peptide synthesizer. Steward and Young, *Solid Phase Peptide Synthesis* (Freeman 1969) and B. Merrifield, *Peptides: Synthesis, Structures, and Applications* (B. Gutte, Ed., Acedemic Press 1995). In this procedure a protected amino acid bearing $R_1$ or protected $R_1$ is bound to a resin support. The resin support employed can be any suitable resin conventionally employed in the art for the solid phase preparation of poly-peptides, preferably polystyrene which has been crossed away with about 0.5 to about 3 percent divinyl benzene, which has been either in chloromethylated or hydroxymethylated to provide sites for ester formation with the initially introduced protected amino acid. Suitable resins are well known and appreciated in the art, including those described in Rink, *Tet. Let.*, 28, 3787 (1987) and Sieber, *Tet. Let.*, 28, 2107 (1987). Included within the solid phase methods are combinatorial methods which are known in the art. K. S. Lam, *Chem. Rev.*, 97, 411–448 (1997).

In a subsequent step the resin-bound protected amino acid is sequentially amino deprotected and coupled with a protected amino acids bearing $R_2$ or protected $R_2$ to give a resin-bound protected dipeptide. This resin bound protected dipeptide is sequentially amino deprotected and coupled with a protected amino acid bearing $R_3$ or protected $R_3$ to give a protected tripeptide. Alternately, an appropriate protected dipeptide may be coupled by the solution method prior to coupling with the resin-bound amino acid.

Each protected amino acids or amino acid sequence is introduced into the solid phase reactor and about a two-fold to four-fold excess. The coupling is carried out in a suitable medium, for example dimethylformamide, dichloromethane, or mixtures of dimethylformamide and dichloromethane. As is well known and appreciated in the art, wherein complete coupling occurs, the coupling in procedure is repeated before removal of the protecting group, prior to the coupling of the next amino acids in the solid phase reactor.

After the compound of formula (1) or protected compound of formula (1) has been obtained it is removed from the resin under conditions well known in the art. For example, removal can be accomplished by treatment of the resin bound compound with a solution of 5% anisole in anhydrous hydrofluoric acid, 95% trifluoroacetic acid/4% water/1% 2-mercaptoethanol solution, or other procedures as are appropriate depending on the resin used.

Compounds of formula (1) obtained by solid phase sequential procedures can be purified by procedures well known and appreciated in the art, such as chromatography, lyophilzation, trituration, salt formation, and crystallization.

The compounds of formula (1) can also be prepared by solution phase sequential procedures well known and appreciated in the art. Accordingly, suitably protected amino acids, substituted acids or dipeptides are coupled by procedures requiring activation of the carbonyl group and coupling reaction with amine function of an appropriate protected amino acid or dipeptide. These procedures are well known appreciated in the art.

Specifically, a carbonyl protected amino acid bearing $R_1$ or protected $R_1$ is coupled with an amino protected amino acid bearing $R_2$ or protected $R_2$, followed by a selective amino deprotection, and coupling with an acid bearing $R_3$ or protected $R_3$ and —$SR_4$, or a functionality which gives rise to —$SR_4$ upon deprotection and modification or displacement and further modification, if desired. Alternately, a carbonyl protected dipeptide bearing a $R_1$ or protected $R_1$ amino acids residue at the carbonyl end a $R_2$ or protected $R_2$ amino acids residue at amino end is coupled an amino protected amino acid bearing $R_3$ or protected $R_3$ and —$SR_4$, or a functionality which gives rise to —$SR_4$ upon deprotection and modification or displacement and further modification, if desired.

The selection of an appropriate coupling reagent is within the skill of the art. A particularly suitable coupling reagent where the amino acid to be added is glutamine, asparingine, or aspratamine is N,N'-diisopropylcarbodiimide and 1-hydroxy-benzotriazole. The use of these reagents prevents nitrile and lactam formation. Other coupling agents are carbodiimides (e.g., N,N'-dicyclohexylcarbodiimide and N-ethyl-N'-(3-dimethylaminopropylcarbodiimide); cyanamides (e.g., N,N-dibenzylcyanamide); (3) ketenimines; isoxazolium salts (e.g., N-ethyl-5-phenyl-isoxazolium-3'-sulfonate; monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; alkoxylated acetylene (e.g., ethoxyacetylene); reagents which form a mixed anhydride with the carboxyl moiety of the amino acid (e.g., ethylchloroformate and isobutylchloroformate) or the symmetrical anhydride of the amino acid to be coupled (e.g., Boc-phenylalanine-O-phenylalinine-Boc) and nitrogen containing heterocyclic compounds having a hydroxy group on one ring nitrogen (e.g., N-hydroxyphthalimide, N-hydroxysuccinimide and 1-hydroxybenzotriazole). Other activating reagents and their use in peptide coupling are described by Kapoor, *J. Pharm. Sci.*, 59, 1–27 (1970). When using the solid phase method, Applicants prefer the use of use of the symmetrical anhydride as a coupling reagent for all amino acids except arginine, asparamine and glutamine.

In coupling individual amino acids, substituted acids, or peptides as described above the selection and use of appropriate protecting groups for $R_1$, $R_2$, $R_3$, or the thiol ultimately bearing $R_4$ is within the ability of those skilled in the art and will depend on the amino acid to be protected in the presence of other protected amino acids residues, thiol protecting groups, and subsequent displacement or modification reactions as are required.

In carrying out the procedures described herein, suitable protecting groups with each amino acid introduced may be any of amino acid protecting groups known in the art. Suitable amino protecting groups include, acyl type protecting groups such as: formyl, trifluoroacetyl, 4-chlorobutyryl, phthalyl, and o-nitrophenoxyacetyl and, sulfonyl type protecting groups such as toluenesulfonyl(tosyl), benzenesulfonyl, nitro-phenylsulfenyl, and tritylsulfenyl; aromatic urethane type protecting groups such as benzyloxycarbonyl and substituted benzyloxycarbonyl, such as p-chlorobenzyloxycarbonyl, p-nitrobenzyloxycarbonyl, p-bromobenzyl-oxycarbonyl, p-methoxybenzyloxycarbonyl, 1-(p-biphenylyl)-1-methylethoxycarbonyl, and benzhydryloxycarbonyl; aliphatic urethane protecting groups such as tert-butyloxycarbonyl(t-Boc), diisopropylmethoxycarbonyl, isopropyloxycarbonyl, ethoxycarbonyl and allyloxycarbonyl; cycloalkyl urethane type protecting groups such as cyclopentyloxycarbonyl, adamantyloxycarbonyl, and cyclohexyloxycarbonyl; thio urethane type protecting groups such as phenylthiocarbonyl; alkyl type protecting groups such as triphenylmethyl(trityl) and benzyl; and trialkylsilane groups such as trimethylsilane. The preferred amino protecting group is tert-butyloxycarbonyl.

As is appreciated by those skill in the art, many of the amino acids require protection during such sequential procedures. The use and selection of appropriate protecting groups is within the ability of those skilled in the art and will depend upon them amino acid to be protected in the presence of other protected amino acid residues or other protecting groups. For example, the selection of such a side chain protecting group is critical in that it must be one which is not removed during cleavage of the protecting group of the amino moiety. For example, the carboxylic group of aspartic acid and glutamic acid can be protected with a benzyl or cyclohexyl group. The preferred protecting group is benzyl. For example, when t-Boc is used as the a-amino protecting group, the following side chain protecting groups are suitable: p-toluenesulfonyl can be used to protect amino containing side chain; p-methoxybenzyl, benzyl, acetyl, benzoyl, t-butylsulfonyl moieties can be used to protect thiol containing side chains; benzyl and cyclohexyl can be used to protect carboxylic acid containing side chains; benzyl can be used to protect the hydroxy of hydroxyalkyl containing side chains, and 2-bromocarbobenzyloxy can be used to protect the hydroxy of hydroxyaromatic containing side chains.

The compounds of formula (1) can be prepared by utilizing techniques and procedures well known and appreciated by one of ordinary skill in the art. To further illustrate, general synthetic schemes for preparing intermediates and the compounds of formula (1) are set forth below. In the reaction schemes below, the reagents and starting materials are readily available to one of ordinary skill in the art and all substituents are as previously defined unless otherwise indicated.

Reaction Scheme A

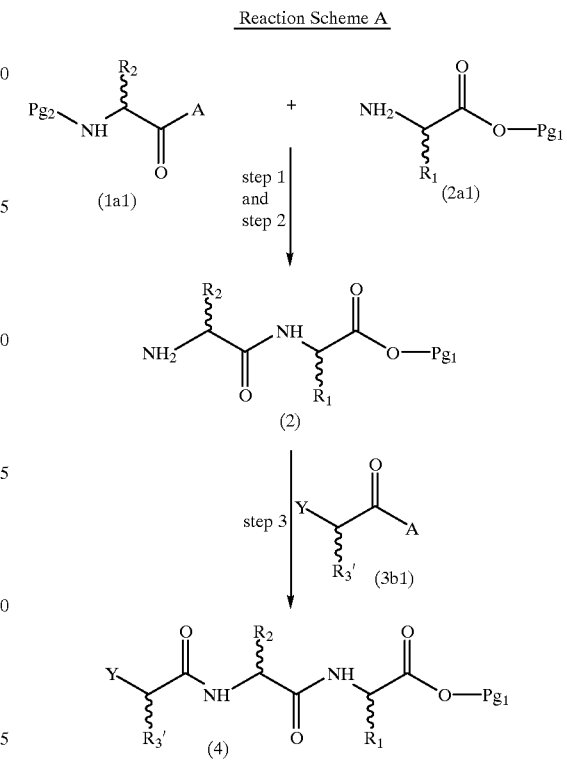

In Scheme A, step 1, an appropriate amino protected amino acid derivative of the formula (1a1) or a salt thereof is coupled with an appropriate carboxy protected amino acid of the formula (2a1) to give, after amino deprotection (step 2), a dipeptide of formula (2).

An appropriate compound of the formula (1a1) is one in which $R_2$ is as desired in the final compound of formula (1) or gives rise after deprotection to $R_2$ as desired in the final compound of formula (1). In addition, an appropriate compound of the formula (1a1) may also be one in which the stereochemistry at the $R_2$ bearing carbon is as desired in the final product of formula (1). The amino protecting group ($Pg_2$) is one which can be selectively removed in the presence of $Pg_1$ and any protecting groups on $R_1$ and/or $R_2$. The use of t-Boc and F-moc for $Pg_2$ is preferred. The activating group (A) is one which undergoes an amidation reaction. As is well known in the art an amidation reaction may proceed through an acid, A is —OH; or an acid may be first converted to an acid chloride, A is —Cl; or an activated intermediate; such as an anhydride; a mixed anhydride of aliphatic carboxylic acid, such as formic acid, acetic acid, propionic acid, butyric acid, isobutyric acid, pivalic acid, 2-ethylbutyric acid, trichloroacetic acid, trifluoroacetic acid, and the like; of aromatic carboxylic acids, such as benzoic acid and the like; of an activated ester, such as phenol ester, p-nitrophenol ester, 2,4-dinitrophenol ester, pentafluorophenol ester, pentachlorophenol ester, N-hydroxysuccinimide ester, N-hydroxyphthalimide ester, 1-hydroxy-1H-benztriazole ester, and the like; activated amide, such as imidazole, dimethylpyrazole, triazole, or tetrazole; or an intermediate formed in the presence of coupling agents, such as dicyclohexylcarbodiimide or 1-(3-dimethylaminopropyl)-3-ethylcarbodiimide. Acid chlorides and activated intermediates may be prepared but are not necessarily isolated before the addition of an appropriate amine of formula (1a1) or a salt thereof.

An appropriate compound of the formula (2a1) is one in which $R_1$ is as desired in the final compound of formula (1) or gives rise after deprotection to $R_1$ as desired in the final compound of formula (1). In addition, an appropriate compound of formula (2a1) may also be one in which the stereochemistry at the $R_1$ bearing carbon is as desired in the final product of formula (1). The carboxy protecting group ($Pg_1$) is one which allows for selective removal of the amino protecting group ($Pg_2$) and does not interfere with subsequent deprotection, displacement, derivitivization, functionalization, or modification reactions, as are required. The carboxy protecting group ($Pg_1$) may also be an attachment to a suitable resin. For solution phase couplings the use of the carboxy protecting groups, such as methyl, t-butyl, cyclohexyl, benzyl, and diphenylmethyl are preferred.

Such peptide coupling reactions are carried out in suitable solvents and using suitable bases and coupling reagents, as required, and are well known and appreciated in the art. The product of Reaction Scheme A, step 1, can be isolated and purified by techniques well known in the art, such as extraction, evaporation, trituration, lyophilization, chromatography, and recrystallization. Alternately, the product of Reaction Scheme A, step 1, can be used directly in step 2 after isolation and without further purification.

In Reaction Scheme A, step 2, the amino protecting group ($Pg_2$) of the product of coupling step 1 is selectively removed to give the dipeptide of formula (2). Such selective amino deprotection reactions are well known and appreciated in the art. The product of Reaction Scheme A, step 2, can be isolated and purified by techniques well known in the art, such as extraction, evaporation, salt formation, trituration, lyophilization, chromatography, and recrystallization.

In Reaction Scheme A, step 3, a dipeptide of formula (2) coupled with an appropriate acid derivative bearing $R_{3'}$ and Y (compound of formula (3b1)) to give a compound of formula (4). Such coupling reactions are well known and appreciated in the art and discussed above. The product of Reaction Scheme A, step 3, can be isolated and purified by techniques well known in the art and described in Reaction Scheme A, step 1, above.

An appropriate compound of formula (3b1) is one in which $R_{3'}$ is $R_3$ as desired in the final product of formula (1) or gives rise after deprotection to $R_3$ as desired in the final product of formula (1) and Y is a protected thio substituent or Y may be a protected hydroxy substituent or bromo which gives rise upon selective deprotection and displacement or displacement and further deprotection and/or elaboration, if required, to —$SR_4$ as desired in the final product of formula (1) (Reaction Scheme C). Alternately, an appropriate compound of formula (3b1) may also be one in which $R_{3'}$ gives rise to $R_{3''}$ which, upon derivatization, gives rise $R_3$ as desired in the final product of formula (1) and Y is a protected thio substituent. The activating group (A) is as described in Reaction Scheme A, step 1, above (Reaction Scheme D). In addition, an appropriate compound of formula (3b1) may also be one in which the stereochemistry at the $R_{3'}$ and Y bearing carbon is as desired in the final product of formula (1) or gives rise after displacement to the stereochemistry as desired at that carbon in the final product of formula (1).

The use and selection of appropriate protecting groups is within the ability of those skilled in the art and will depend upon compound of formula (3b1) to be protected, the presence of other protected amino acid residues, other protecting groups, and the nature of the particular $R_3$ and/or $R_4$ group(s) ultimately being introduced. Compounds of formula (3b1) in which Y is bromo and protected thio are commercially available or can be prepared utilizing materials, techniques, and procedures well known and appreciated by one of ordinary skill in the art or described herein. See PCT Application WO 96/11209, published Apr. 18, 1996. Examples commercially available compounds of formula (3b1) in which Y is bromo include 2-bromopropionic acid, 2-bromobutyric acid, 2-bromovaleric acid, 2-bromohexanoic acid, 6-(benzoylamino)-2-bromohexanoic acid, 2-bromoheptanoic acid, 2-bromooctanoic acid, 2-bromo-3-methylbutyric acid, 2-bromoisocaproic acid, 2-bromo-3-(5-imidazoyl)proionic acid, (R)-(+)-2-bromopropionic acid, (S)-(−)-2-bromopropionic acid.

In addition, an appropriate compound of formula (3b1) may also be one in which the stereochemistry at the $R_3$ and Y bearing carbon is as desired in the final product of formula (1) or gives rise after displacement to the stereochemistry as desired at that carbon in the final product of formula (1). The activating group (A) is as described in Reaction Scheme A, step 1, above.

The versatile intermediate of formula (4) can also be prepared as set forth below in Reaction Scheme B.

Reaction Scheme B

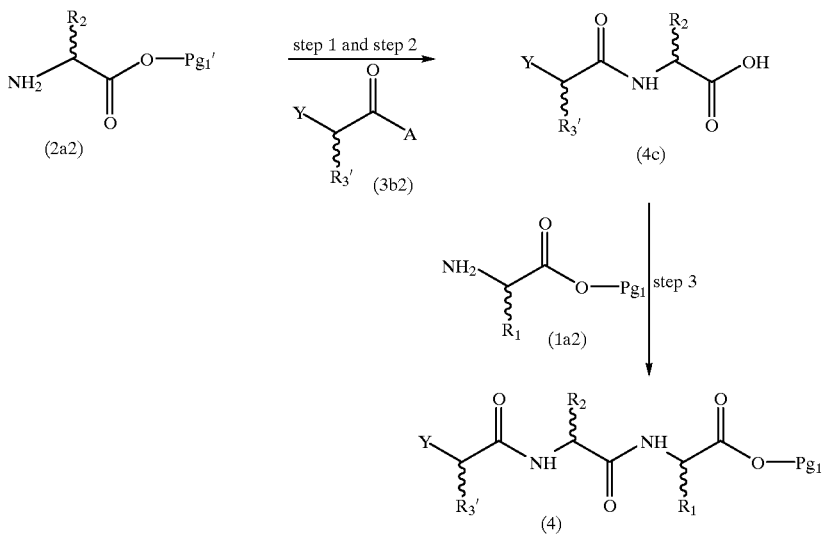

In Scheme B, step 1, an appropriate carboxy protected amino acid derivative bearing $R_2$ or protected $R_2$ (compound of the formula (2a2)) is coupled with an appropriate acid derivative bearing $R_{3'}$ and Y (compound of formula (3b2)), to give after carboxy deprotection (step 2), a compound of formula (4c). Such coupling reactions are carried out in suitable solvents and using suitable bases and coupling agents, as required, and are well known and appreciated in the art and discussed above. The product of Reaction Scheme B, step 1, can be isolated and purified by techniques well known in the art or can be used directly in step 2.

An appropriate compound of the formula (2a2) is one in which $R_2$ is as desired in the final compound of formula (1) or gives rise after deprotection to $R_2$ as desired in the final compound of formula (1). In addition, an appropriate compound of the formula (2a2) may also be one in which the stereochemistry at the $R_2$ bearing carbon is as desired in the final product of formula (1). The carboxy protecting group ($Pg_{1'}$) is one which can be selectively removed in the presence of any protecting groups on $R_2$, $R_{3'}$, and/or Y. The use of methyl, benzyl, and t-butyl for $Pg_{1'}$ is preferred.

An appropriate compound of formula (3b2) is one in which $R_{3'}$ and Y are as defined in Reaction Scheme A, step 3, above. In addition, an appropriate compound of formula (3b2) may also be one in which the stereochemistry at the $R_{3'}$ and Y bearing carbon is as desired in the final product of formula (1) or gives rise after displacement to the stereochemistry as desired at that carbon in the final product of formula (1). The activating group (A) is as described in Reaction Scheme A, step 1, above.

In Reaction Scheme B, step 2, the carboxy protecting group ($Pg_{1'}$) of the product of coupling step 1 is selectively removed to give the compound of formula (4c). Such selective carboxy deprotection reactions are well known and appreciated in the art. The product of Reaction Scheme B, step 2, can be isolated and purified by techniques well known in the art, such as extraction, evaporation, salt formation, trituration, lyophilization, chromatography, and recrystallization or can be used directly in the following step.

In Reaction Scheme B, step 3, an appropriate carboxy protected amino acid derivative bearing $R_1$ or protected $R_1$ (compound of the formula (1 a2)) is coupled with a compound of formula (4c) to give a compound of formula (4). Such coupling reactions are carried out as discussed above.

An appropriate compound of the formula (1a2) is one in which $R_1$ is as desired in the final compound of formula (1) or gives rise after deprotection to $R_1$ as desired in the final compound of formula (1). In addition, an appropriate compound of formula (1a2) may also be one in which the stereochemistry at the $R_1$ bearing carbon is as desired in the final product of formula (1). The carboxy protecting group ($Pg_1$) is as defined in Reaction Scheme A, step 1.

In Reaction Scheme C an intermediate of formula (4) in which $R_{3'}$ is $R_3$ as desired in the final product of formula (1) or gives rise after deprotection to $R_3$ as desired in the final product of formula (1) and Y is a protected thio substituent or a hydroxy substituent or bromo gives rise to a final product of formula (1).

Reaction Scheme C

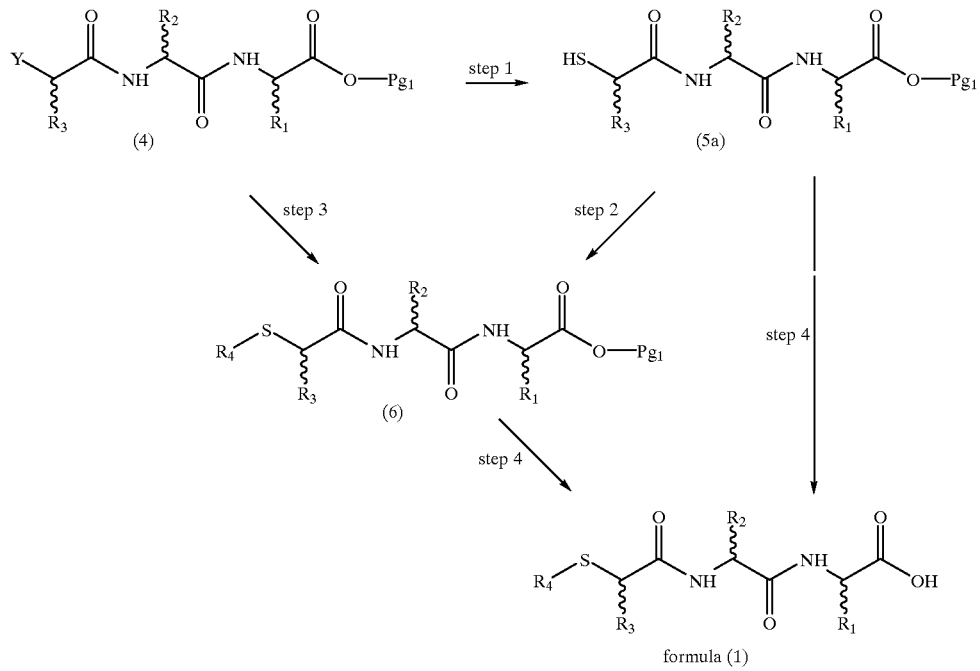

In Reaction Scheme C, step 1, a compound of formula (4) in which Y is protected thio gives rise upon selective deprotection to give a compound of formula (5a).

For example, compounds of formula (4) in which Y is a protected thio substituent, are selectively deprotected to give a thiol of formula (5a). Protected thio substituents include thioesters, such as thioacetyl or thiobenzoyl, thioethers, such as thiobenzyl, thio-4-methoxybenzyl, thiotriphenylmethyl, or thio-t-butyl, or unsymmetrical sulfides, such as dithioethyl or dithio-t-butyl. The use and selective removal of such thio protecting groups is well known and appreciated in the art and described in *Protective Groups in Organic Synthesis*, Theodora W. Greene (Wiley-Interscience, 2nd Edition, 1991).

Also encompassed by Reaction Scheme C, step 1, a compound of formula (4) in which Y is hydroxy (obtained from protected hydroxy compounds of formula (4)) undergoes a displacement reaction with an appropriate thio introducing reagent by the method of Mitsunobu to give a compound of formula (4) in which Y is a protected thio substituent or —$SR_4$ as desired in the final compound of formula (1). For example, a compound of formula (4) in which Y is hydroxy reacts with thioacetic acid or thiobenzoic acid, triphenylphosphine, and diethylazodicarboxylate in a suitable aprotic solvent, such as tetrahydrofuran to give a compound of formula (4) in which Y is thioacetyl or thiobenzoyl. Selective removal of the thioacetic acid or thiobenzoic acid moiety gives the desired compound of formula (5a). The product can be isolated and purified by techniques well known in the art, such as extraction, evaporation, trituration, lyophilization, chromatography, and recrystallization.

Also, in Reaction Scheme C, step 1, a compound of formula (4) in which Y is bromo undergo a displacement reaction with an appropriate thio introducing reagent to give a compound of formula (4) in which Y is protected thio substituent which gives rise upon deprotection and subsequent elaboration, if desired, the —$SR_4$ as desired in the final compound of formula (1). An appropriate thio introducing reagent is also one which introduces a group —$SR_4$ as desired in the final compound of formula (1).

For example, a solution of p-methoxybenzylmercaptan in a suitable organic solvent such as dimethylformamide is degassed and treated with a suitable base such as sodium hydride. After about 1 to 2 hours, a solution of a compound of formula (4) in which Y is bromo is added. The reaction may benefit from the addition of a suitable catalyst, such as tetra-n-butylammonium iodide. The reaction mixture is carried out for 1 to 25 hours at temperatures ranging form 0° C. to about 100° C. Selective removal of the 4-methoxybenzyl moiety gives the desired compound of formula (5a). The product can be isolated and purified by techniques well known in the art, such as extraction, evaporation, trituration, lyophilization, chromatography, and recrystallization.

In Reaction Scheme C, step 2, a compound of formula (5a) undergoes modification reaction to give a compound of formula (6). Such modification reactions include, thiol esterification and disulfide formation.

Compounds of formula (6) in which $R_4$ is —C(O)$R_{10}$ or —C(O)—(CH$_2$)$_q$—X group can be synthesized by thiol esterifications according to techniques well known and appreciated by one of ordinary skill in the art, such as those disclosed in U.S. Pat. No. 5,424,425, issued Jun. 13, 1995.

For example, in a thiol esterification a compound of formula (5a) is contacted with about an equimolar amount of an appropriate acid, such as HO—C(O)$R_{10}$ or HO—C(O)—(CH$_2$)$_q$—X in the presence of a suitable coupling agent to give a compound of formula (6) in which $R_4$ is —C(O)$R_{10}$ or —C(O)—(CH$_2$)$_q$—X. The reaction is carried out in the presence of a coupling agent such as 2-fluoro-1-methylpyridinium p-toluenesulfate, EDC (1-(3-dimethylaminopropyl)-3-ethylcarbodiimide hydrochloride), carbonyldiimidazole, EEDQ (1-ethoxycarbonyl-2-ethoxy-1, 2-dihydroquinoline, DCC, or diethylcyanophosphonate in a suitable aprotic solvent such as methylene chloride. The reaction is generally carried out at temperature of between −20° C. and the boiling point of the solvent. Generally, the reaction requires 1 to 24 hours. The product can be isolated and purified by techniques well known in the art, such as extraction, evaporation, trituration, lyophilization, chromatography, and recrystallization.

Compounds of formula (6) in which $R_4$ is —S—G group can be synthesized according to techniques well known and appreciated by one of ordinary skill in the art, as disclosed in PCT Application No. WO 95/21839, published Aug. 17, 1995 and U.S. Pat. No. 5,491,143, issued Feb. 13, 1996, and U.S. Pat. No. 5,731,306, issued Mar. 24, 1998, and Roques, B. P. et al., *J. Med. Chem.* 33, 2473–2481 (1992).

For example, in a disulfide formation a compound of formula (5a) is contacted with an appropriate compound of formula (7).

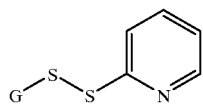

(7)

An appropriate compound of formula (7) is one which gives G as desired in the final product of formula (1) or gives rise upon deprotection to G as is desired in the final product of formula (1). In addition, the compound of formula (7) may have stereochemistry as desired in the final product of formula (1). The reaction is carried out in a suitable solvent, such as ethanol, methanol, dichloromethane, or mixtures of ethanol or methanol and dichloromethane. The solvent is degassed by passing a stream of nitrogen gas through it for 15 minutes before the reaction is carried out. The reaction is carried out using from 1.0 to 4.0 molar equivalents of an appropriate compound of formula (7). The reaction is carried out at temperatures of from 0° C. to the refluxing temperature of the solvent, with a temperature of 10° C. to 30° C. being preferred. The reaction generally requires from 1 to 48 hours. The product can be isolated by techniques well known in the art, such as extraction, evaporation, and precipitation and can be purified by chromatography and recrystallization.

In Reaction Scheme C, step 3, a compound of formula (4) in which Y is hydroxy or bromo can be displaced by an appropriate thiol, $HSR_4$, by the methods described in Reaction Scheme C, step 1, to give a compound of formula (6). In Reaction Scheme C, step 3, an appropriate thiol $HSR_4$ is one which gives $R_4$ as desired in the final product of formula (1) or gives rise to $R_4$ as desired in the final product of formula (1). In addition, a compound of formula (4) in which Y is bromo can be displaced by an appropriate thio ester, $Ph_3S$—$C(O)$—$(CH_2)_q$—X by techniques well known and appreciated in the art, as disclosed in U.S. Pat. No. 5,424,425, issued Jun. 13, 1995.

In Reaction Scheme C, step 4, a compound of formula (5), (5a), or (6) is deprotected to give a compound of formula (1). Such deprotection reactions are well known appreciated in the art and may include selective deprotections in which the carboxy protecting group ($Pg_1$) and protecting groups on $R_1$, $R_2$, $R_3$, and $R_4$ are removed if desired.

In Reaction Scheme D an intermediate of formula (4) in which $R_{3'}$ gives rise to $R_{3''}$ and Y is —$SR_4$ as is desired in the final product of formula (1) or a protected thio substituent gives a compound of formula (1).

Reaction Scheme D

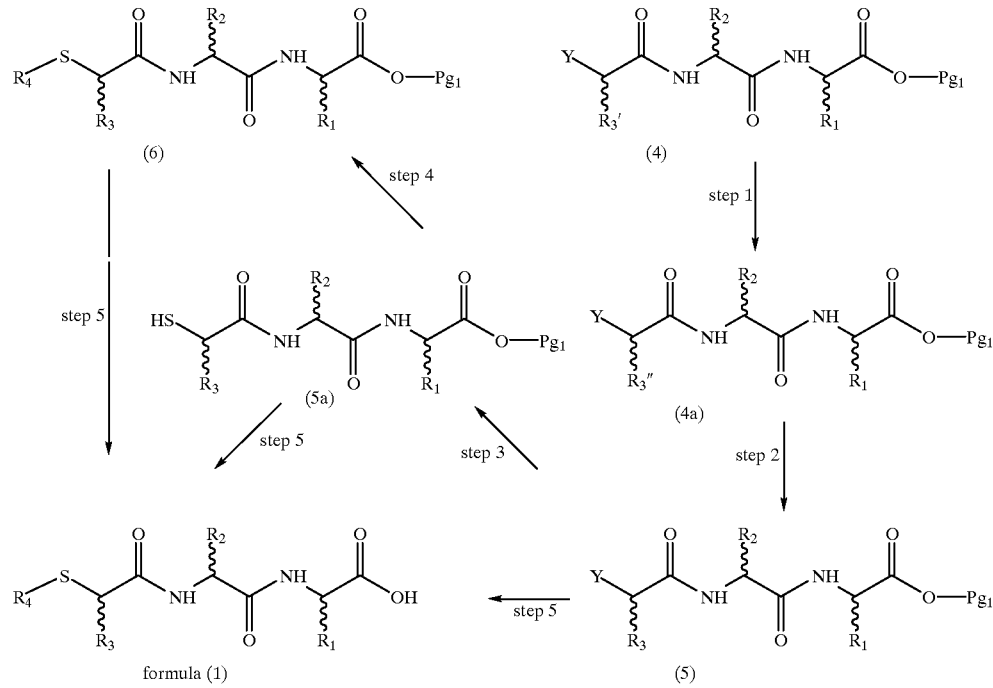

In Reaction Scheme D, step 1, an appropriate compound of formula (4) is deprotected, hydrolyzed, or reduced to give a compound of formula (4a). In Reaction Scheme D, step 1, an appropriate compound of formula (4) is one in which $R_{3'}$ gives rise to a compound of formula (4a) in which $R_{3''}$ is $R_3$ as desired in the final product of formula (1) or undergo further derivitization (step 2) to give a compound of formula (5) in which $R_3$ is a desired in the final product of formula (1). In Reaction Scheme D, step 1, an appropriate compound of formula (4) is one in which Y is —$SR_4$ as desired in the final compound of formula (1) or Y gives rise upon deprotection (step 5) and further functionalization (step 4) to give —$SR_4$, as desired, in the final product of formula (1).

For example, in a deprotection a compound of formula (4) in which $R_{3'}$ is —$(CH_2)_m$—W (phthalimido group) is contacted with a molar excess of hydrazine monohydrate to give a compound of formula (4a) in which $R_{3''}$ is —$(CH_2)_m$—$NHR_8$ in which $R_8$ is hydrogen. The reaction is typically carried out in a protic organic solvent, such as methanol or ethanol. The reaction is generally carried out at room temperature for a period of time ranging from 5–24 hours. The product can be isolated by techniques well known in the art, such as extraction, evaporation, and precipitation and can be purified by chromatography and recrystallization.

Alternately, for example, in a deprotection a compound of formula (4) in which $R_{3'}$ is —$(CH_2)_m$—$NR_8$-t-Boc is contacted with a molar excess of a suitable acid to give a compound of formula (4a) in which $R_{3''}$ is —$(CH_2)_m$—$NHR_8$. The reaction is typically carried out in a organic solvent, such as methanol, ethanol, ethyl acetate, diethyl ether, or dioxane. Suitable acids for this reaction are well known in the art, including hydrochloric acid, hydrobromic acid, trifluoroacetic acid, and methanesulfonic acid. The reaction is generally carried out at room temperature for a period of time ranging from 1–10 hours. The product can be isolated by techniques well known in the art, such as extraction, evaporation, and precipitation and can be purified by chromatography and recrystallization.

For example, in a hydrolysis a compound of formula (4) in which $R_{3'}$ is —$(CH_2)_m$—$C(O)OPg_3$ and $Pg_3$ is methyl or ethyl is contacted with about 1 to 2 molar equivalents of lithium hydroxide, sodium hydroxide, or potassium hydroxide to give a compound of formula (4a) in which $R_{3''}$ is —$(CH_2)_m$—$CO_2H$. The reaction is carried out in a suitable solvent, such as methanol, ethanol methanol/water mixtures, ethanol/water mixtures, or tetrahydrofuran/water mixtures and generally requires 1 to 24 hours. The reaction is carried out at temperatures of from about 0° C. to the refluxing temperature of the solvent. The resulting acid is isolated and purified by techniques well known in the art, such as acidification, extraction, evaporation, and precipitation and can be purified by trituration, precipitation, chromatography, and recrystallization.

For example, in a reduction a compound of formula (4a) in which $R_{3'}$ is —$(CH_2)_{m-1}$—$CO_2Pg_3$ in which $Pg_3$ is methyl or ethyl is contacted with a suitable reducing agent, such as lithium borohydride, lithium aluminum hydride, diisobutylaluminum hydride, 9-borabicyclo[3.3.1]nonane, preferably lithium borohydride to provide a compound of formula (4a) in which $R_{3''}$ is —$(CH_2)_{m-1}$—$CH_2OH$. The reaction is carried out in a suitable solvent, such as dichloromethane, tetrahydrofuran, or toluene, with tetrahydrofuran being preferred. The reaction is carried out at a temperature of from about −30° C. to about 50° C. and generally requires from 2 to 12 hours. The product can be isolated by quenching, extraction, evaporation, and precipitation and can be purified by trituration, chromatography, and recrystallization.

In Reaction Scheme D, step 2, a compound of formula (4a) undergoes a derivitization reaction to give a compound of formula (5) in which $R_3$ is as desired in the final product of formula (1). Such derivitization reactions include hydrolysis of esters and ester formations as are well known in the art, ether formation, amine alkylation, formation of amides, urea formation, carbamate formation, and formation of sulfonamide. In Reaction Scheme D, step 2, the compound of formula (4a) is one in which Y is a protected thio group, such as thioacetyl, thiobenzoyl, 4-methoxybenzyl thiol or t-butylthiol.

For example, in an ether formation a compound of formula (4a) in which $R_{3''}$ is —$(CH_2)_{m-1}$—$CH_2OH$ is contacted with 1 to 10 molar equivalents of a suitable akylating agent to give a compound of formula (5) in which $R_3$ is —$(CH_2)_m$—Z—Q in which Z is —O—. A suitable alkylating agent is one which transfers Q or protected Q as desired in the final product of formula (1), such as benzyl bromide, benzyl chloride, substituted benzyl bromide, substituted benzyl chloride, ethyl bromoacetate, t-butyl bromoaceate, ethyl 3-chloropropionate, ethyl 3-bromopropionate, ethyl 5-bromovalerate, ethyl 4-bromobutyrate, 3-chloropropionamide, 2-bromoethylbenzene, substituted 2-bromoethylbenzene, 1-chloro-3-phenylpropane, 1-bromo-4-phenylbutane, and the like, or nitrogen mustards, including 2-dimethylaminoethyl chloride, 2-diethylaminoethyl chloride, and 3-dimethylaminopropyl chloride. The reaction is carried out in a suitable solvent, such as diethyl ether, tetrahydrofuran, dimethylformamide, dimethyl sulfoxide, or acetonitrile and using a suitable base, such as sodium hydride, potassium hydride, potassium t-butoxide, and lithium diisopropylamide. The reaction is generally carried out at temperatures of −70° C. and room temperature and require from about 1–24 hours. The product can be isolated by techniques well known in the art, such as extraction, evaporation, and precipitation and can be purified by chromatography and recrystallization.

Alternately, as appreciated by those skilled in the art, an ether formation can also be carried out by a procedure similar to the one above using a compound of formula (4a) in which $R_{3''}$ is —$(CH_2)_{m-1}$—$CH_2OH$ in which the hydroxy group is first converted to a leaving group, such as chloro, bromo, or mesylate and a suitable alcohol which transfers Q or protected Q as desired in the final product of formula (1), such as benzyl alcohol, substituted benzyl alcohol, phenol, substituted phenol, and the like. The conversion of hydroxy to leaving groups, such as chloro, bromo, and mesylate are well known and appreciated in the art.

For example, in an amine alkylation a compound of formula (4a) in which $R_{3''}$ is —$(CH_2)_m$—$NHR_8$ is contacted with 1 to 10 molar equivalents of a suitable alkylating agent to give a compound of formula (5) in which $R_3$ is —$(CH_2)_m$—Z—Q in which Z is —$NR_8$—. The reaction may be carried out after protection of the amine function of $R_{3''}$ in which $R_8$ is hydrogen by a suitable protecting group, such as benzyl or t-Boc. For an amine alkylation a suitable alkylating agent is one as described above for the ether formation and also includes alkylhalides, such as methyl iodide, methyl bromide, ethyl bromide, propyl bromide, propyl chloride, butyl bromide, butyl chloride, and the like. The reaction is carried out in a suitable solvent, such as methanol, ethanol, dimethylformamide, or pyridine and using a suitable base, such as sodium carbonate, triethylamine, N,N-diisopropylethylamine or pyridine. The reaction is generally carried out at temperatures of room temperature to the refluxing temperature of the solvent and require from about 1–24 hours. The product can be isolated by techniques well known in the art, such as extraction, evaporation, and precipitation and can be purified by chromatography and recrystallization.

Alternately, for example, in an amine alkylation a compound of formula (4a) in which $R_{3''}$ is —$(CH_2)_m$—$NHR_8$ is contacted in a reductive alkylation with a suitable aldehyde to give a compound of formula (5) in which $R_3$ is —$(CH_2)_m$—Z—Q in which Z is —$NR_8$—. A suitable aldehyde is one which transfers Q or protected Q as desired in the final product of formula (1), such as benzaldehyde and substituted benzaldehydes, The reaction is carried out in a suitable solvent, such as methanol, ethanol, tetrahydrofuran, or mixtures of methanol or ethanol and tetrahydrofuran. The reaction may be carried out in the presence of a drying agent, such as sodium sulfate or molecular sieves. The reaction is carried out in the presence of from 1.0 to 6.0 molar equivalents of a suitable reducing agent, such as, sodium borohydride or sodium cyanoborohydride with sodium cyanoborohydride being preferred. It may be advantageous to maintain the pH in the range of about 4 to 6. The reaction is generally carried out at temperatures of from 0° C. to the refluxing temperature of the solvent. Generally, the reactions require 1 to 72 hours. The product can be isolated by techniques well known in the art, such as extraction, evaporation, and precipitation and can be purified by chromatography and recrystallization.

For example, in an amido formation a compound of formula (4a) in which $R_{3''}$ is is —$(CH_2)_m$—$CO_2H$ is contacted with a suitable amine in an amide formation to give a compound of formula (5) in which $R_3$ is —$(CH_2)_m$—Z—Q in which Z is amido. Such amide formation reactions using carboxy activation or suitable coupling agents are well known in the art and described above. A suitable amine, $HNR_8Q$, gives rise to $R_8$ and Q as desired in the final product of formula (1), such as methylamine, ethylamine, propylamine, butylamine, N-methyl benzylamine, benzyl β-alanine, 4-(3-aminopropyl)morpholine, and the like.

For example, in an amide formation a compound of formula (4a) in which $R_{3''}$ is is —$(CH_2)_m$—$NHR_8$ is contacted with a suitable carboxylic acid in an amide formation to give a compound of formula (5) in which $R_3$ is —$(CH_2)_m$—Z—Q in which Z is amide. Such amide formation reactions using carboxy activation or suitable coupling agents are well known in the art and described above. Suitable carboxylic acids, QC(O)—OH, are ones give rise to Q as desired in the final product of formula (1), such as benzoic acid, substituted benzoic acids, phenyl acetic acids, substituted phenylacetic acids, mono-t-butyl malonate, and the like.

For example, in a urea formation a compound of formula (4a) in which $R_{3''}$ is is —$(CH_2)_m$—$NHR_8$ is contacted with an appropriate isocyanate, O=C=N—Q, to give a compound of formula (5) in which $R_3$ is —$(CH_2)_m$—Z—Q in which Z is urea. An appropriate isocyanate is one which gives rise to Q as desired in the final product, such as phenyl isocyanate, substituted phenyl isocyanate, napthyl isocyanate, ethyl isocyanatoacetate, and the like. The reaction is carried out by adding an equivalent of, or a slight molar excess of, an appropriate isocyanate is added to a solution of a compound of formula (4a) in which $R_{3''}$ is —$(CH_2)_m$—$NHR_8$ in a suitable solvent, such as diethyl ether, benzene, or toluene. The reaction is carried out at temperature of from about 0° C. to the refluxing temperature of the solvent and require about 1–24 hours. The product can be isolated and purified by techniques well known in the art, such as filtration, extraction, evaporation, trituration, chromatography, and recrystallization.

For example, in an N-carbamoyl formation a compound of formula (4a) in which $R_{3''}$ is —$(CH_2)_m$—$NHR_8$ is contacted with an appropriate chloroformate to give a compound of formula (5) in which $R_3$ is —$(CH_2)_m$—Z—Q in which Z is N-carbamoyl. An appropriate chloroformate is one which gives rise to Q as desired in the final product of formula (1). Examples of chloroformates include benzyl chloroformate, naphthyl chloroformate, phenyl chloroformate, and substituted phenyl chloroformates, such as 4-chlorophenyl chloroformate, 4-methylphenyl chloroformate, 4-bromophenyl chloroformate, 4-fluorophenyl chloroformate, 4-methoxyphenyl chloroformate and the like. The reaction is carried out by adding an equivalent of, or a slight molar excess of, an appropriate chloro formate to a solution of a compound of formula (4a) in which $R_{3''}$ is —$(CH_2)_m$—$NHR_8$ in a suitable solvent, such as toluene, tetrahydrofuran, dimethylformamide, dichloromethane, pyridine, or chloroform. The reaction is carried out in the presence of an excess of a suitable base, such as triethylamine, sodium carbonate, potassium bicarbonate, pyridine or N,N-diisopropylethylamine. The reaction is carried out at a temperature of from −70° C. to the refluxing temperature of the solvent and generally requires from 30 minutes to 24 hours. The product can be isolated and purified by techniques well known in the art, such as extraction, evaporation, chromatography, and recrystallization.

For example, in an O-carbamoyl formation a compound of formula (4a) in which $R_{3''}$ is —$(CH_2)_{m-1}$—$CH_2OH$ is contacted with an appropriate isocyanate, as defined above for urea formation, to give a compound of formula (5) in which $R_3$ is —$(CH_2)_m$—Z—Q in which Z is O-carbamoyl. The reaction is carried out in a suitable solvent, such as diethyl ether, tetrahydrofuran, dimethylformamide, or acetonitrile. The reaction may be facilitated by the use of catalytic amount of a suitable base, such as sodium hydride, potassium hydride, or potassium t-butoxide. The reaction is generally carried out at temperatures of from −20° C. to room temperature and require from about 1–24 hours. The product can be isolated by techniques well known in the art, such as extraction, evaporation, and precipitation and can be purified by chromatography and recrystallization.

For example, in a sulfonamide formation to prepare a compound in which $R_3$ is —$(CH_2)_m$—$SO_2NR_8$—$Y_1$, a compound of formula (4a) in which $R_{3''}$ is —$(CH_2)_m$—$NHR_8$ is contacted with an appropriate sulfonamide forming reagent. An appropriate sulfonamide forming reagent, such as a sulfonyl chloride, $Y_1S(O)_2Cl$, or sulfonyl anhydride, $Y_1(O)_2S$—O—$S(O)_2$ $Y_1$, is one which gives rise to $Y_1$ as desired in the final product. Examples of appropriate sulfonamide forming reagents are, benzenesulfonyl chloride, 1-napthalenesulfonyl chloride, 2-napthalenesulfonyl chloride, dansyl chloride, N-morpholinylsulfonyl chloride, N-piperidinylsulfonyl chloride, 2,4,5-trichlorobenzenesulfonyl chloride, 2,5-dichlorobenzenesulfonyl chloride, 2,4,6-triisopropylbenzenesulfonyl chloride, 2-mesitylenesulfonyl chloride, 4-bromobenzenesulfonyl chloride, 4-fluorobenzenesulfonyl chloride, 4-chlorobenzenesulfonyl chloride, 4-methoxybenzenesulfonyl chloride, 4-t-butylbenzenesulfonyl chloride, p-toluenesulfonyl chloride, 2,3,4-trichlorobenzenesulfonyl chloride, 2,5-dimethoxybenzenesulfonyl chloride, 4-ethylbenzenesulfonyl chloride, 3,4-dimethoxybenzenesulfonyl chloride, 2,6-dichlorobenzenesulfonyl chloride, 3-bromobenzenesulfonyl chloride, 4-n-butylbenzenesulfonyl chloride, benzenesulfonic anhydride, 4-toluenesulfonic anhydride, and 2-mesitylenesulfonic anhydride. The reaction is carried out in a suitable solvent, such as tetrahydrofuran, dichloromethane, pyridine, or chloroform and in the presence of an excess of a suitable base, such as triethylamine, sodium carbonate, pyridine, or N,N-diisopropylethylamine. The reaction is carried out at a temperature of from −50° C. to the refluxing temperature of the solvent. The reaction generally requires from 30 minutes to 24 hours. The product can be isolated and purified by techniques well known in the art, such as extraction, evaporation, chromatography, and recrystallization.

In Reaction Scheme D, step 3, a compound of formula (5) in which $R_3$ is as desired in the final product of formula (1) undergoes a selective thiol deprotection to give a compound of formula (5a). Such selective thiol deprotections using suitable protecting groups are well known and appreciated in the art as discussed in Reaction Scheme C, step 1, above.

In Reaction Scheme D, step 4, a compound of formula (5a) undergoes a modification reaction to give a compound of formula (6) as described in Reaction Scheme C, step 2, above.

In Reaction Scheme D, step 5, a compound of formula (5), (5a), or (6) is deprotected to give a compound of formula (1) as discussed in Reaction Scheme C, step 4, above.

Alternate routes to the versatile intermediate of formula (6) are set forth below in Reaction Scheme E.

In step 1a, an appropriate compound of formula (3a1) is one in which $R_3$ and $R_4$ are a desired in the final product of formula (1) or gives rise after deprotection to $R_3$ and/or $R_4$ as desired in the final compound formula (1). In addition, an appropriate compound of formula (3a1) may also be one in which the stereochemistry at the $R_3$ and —$SR_4$ bearing carbon is as desired in the final product of formula (1). The activating group (A) is as described in Reaction Scheme A, step 1, above.

In Scheme B, step 1b, an appropriate carboxy protected amino acid derivative bearing $R_2$ or protected $R_2$ (compound of the formula (2a2)) is coupled with an appropriate acid derivative bearing $R_3$ and —$SR_4$ (compound of formula (3a2)), to give after carboxy deprotection (step 2), a compound of formula (4b). Such coupling reactions are carried out as discussed above. The product of Reaction Scheme B, step 1b, can be isolated and purified by techniques well known in the art and described above or can be used directly in step 2b.

In step 1b, an appropriate compound of the formula (2a2) is one in which $R_2$ is as desired in the final compound of formula (1) or gives rise after deprotection to $R_2$ as desired in the final compound of formula (1). In addition, an appropriate compound of the formula (2a2) may also be one

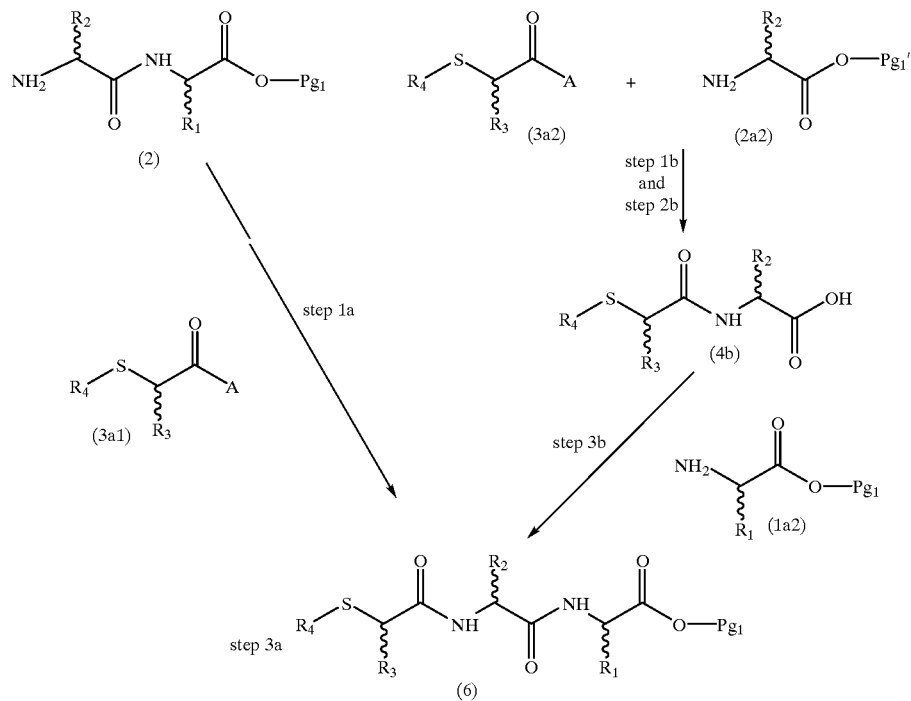

Reaction Scheme E

In Reaction Scheme E, step 1a, a dipeptide of formula (2) is coupled with an appropriate acid derivative bearing $R_3$ and —$SR_4$ (compound of formula (3a1)) to give a compound of formula (6). Such coupling reactions are carried out in suitable solvents and using suitable bases and coupling agents, as required, and are well known and appreciated in the art and discussed above. The product of Reaction Scheme E, step 1a, can be isolated and purified by techniques well known in the art and described in Reaction Scheme A, step 1, above.

in which the stereochemistry at the $R_2$ bearing carbon is as desired in the final product of formula (1). The carboxy protecting group ($Pg_{1'}$) is one which can be selectively removed in the presence of any protecting groups on $R_2$, $R_3$, and/or $R_4$. The use of methyl, benzyl, and t-butyl for $Pg_{1'}$ is preferred. An appropriate compound of formula (3a2) is one in which $R_3$ and $R_4$ are a desired in the final product of formula (1) or gives rise after deprotection to $R_3$ and $R_4$ as desired in the final compound formula (1). In addition, an appropriate compound of formula (3a2) may also be one in which the stereochemistry at the $R_3$ and —$SR_4$ bearing carbon is as desired in the final product of formula (1). The activating group (A) is as described in Reaction Scheme A, step 1, above.

In Reaction Scheme E, the product of step 1b in which Y is bromo preferably undergoes a displacement as described in Reaction Scheme C, steps 1 and 3 to give, after deprotection (step 2) a dipeptide of formula (4b) in which Y is protected thio for use in step 2b and subsequently step 3b.

In Reaction Scheme E, step 2b, the carboxy protecting group ($Pg_1$) of the product of coupling step 1b is selectively removed to give the dipeptide of formula (4b). Such selective carboxy deprotection reactions are well known and appreciated in the art. The product of Reaction Scheme E, step 2b, can be isolated and purified by techniques well known in the art, such as extraction, evaporation, salt formation, trituration, lyophilization, chromatography, and recrystallization or can be used directly in the following step.

In Reaction Scheme E, steps 3b, an appropriate carboxy protected amino acid derivative bearing $R_1$ or protected $R_1$ (compound of the formula (1a2)) is coupled with a dipeptide of formula (4b) to give a compound of formula (6). Such coupling reactions are carried out in suitable solvents and using suitable bases and coupling agents, as required, and are well known and appreciated in the art and discussed above.

An appropriate compound of the formula (1a2) is one in which $R_1$ is as desired in the final compound of formula (1) or gives rise after deprotection to $R_1$ as desired in the final compound of formula (1). In addition, an appropriate compound of formula (1a2) may also be one in which the stereochemistry at the $R_1$ bearing carbon is as desired in the final product of formula (1). The carboxy protecting group ($Pg_1$) is as defined in Reaction Scheme A, step 1, and into account, other protecting groups and subsequent reactions which may be required to provide the final compound of formula (1).

Alternate routes for preparing the compounds of formula (3b1) and formula (3b2) in which Y is bromo are presented in Reaction Schemes F.1 and F.2.

Reaction Scheme F.1

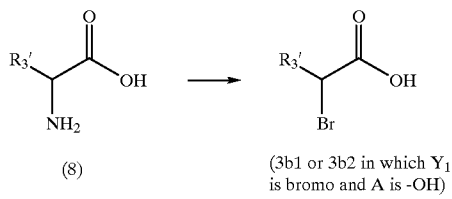

(8)

(3b1 or 3b2 in which $Y_1$ is bromo and A is -OH)

In Reaction Scheme F.1, an appropriate α-amino carboxylic acid of formula (8) is deaminobrominated to give a compound of formula (3b1) or formula (3b2)in which Y is bromo and A is —OH. An appropriate α-amino carboxylic acid of formula (8), and protected forms thereof, is one which is one in which $R_{3'}$ is $R_3$ as desired in the final product of formula (1) or gives rise after deprotection to $R_3$ as desired in the final product of formula (1). In addition, α-amino carboxylic acid of formula (8) may also be one in which the stereochemistry at the $R_{3'}$ bearing carbon gives rise after displacement to the stereochemistry as desired at that carbon in the final product of formula (1). Such appropriate α-amino carboxylic acid of formula (8), are commercially available or may be readily prepared by techniques and procedures well known and appreciated by one of ordinary skill in the art. For example, L-alanine, D-alanine, L-valine, D-valine, D-norvaline, L-leucine, D-leucine, D-isoleucine, D-tert-leucine, glycine, L-glutamic acid, D-glutamic acid, L-glutamine, D-glutamine, L-lysine, D-lysine, L-ornithine, D-ornithine, (D)-(–)-2-aminobutyric acid, D-threonine, D-homoserine, D-allothreonine, D-serine, D-2-aminoadipic acid, D-aspartic acid, D-glutamic acid, D-lysine hydrate, 2,3-diaminopropionic acid monohydrobromide, D-ornithine hydrochloride, D,L-2,4-diaminobutyric acid dihydrochloride, L-meta-tyrosine, D-4-hydroxyphenylglycine, D-tyrosine, L-phenylalanine, D-phenylalanine, D,L-2-fluorophenylalanine, beta-methyl-D,L-phenylalanine hydrochloride, D,L-3-fluorophenylalanine, 4-bromo-D,L-phenylalanine, L-phenylalanine, L-phenylglycine, D-phenylglycine, D,L-4-fluorophenylalanine, 4-iodo-D-phenylalanine, D-homophenylalanine, D,L-2-fluorophenylglycine, D,L-4-chlorophenylalanine, and the like, are all commercially available and the methods in D. A. Evans, et al. *J. Am. Chem. Soc.*, 112, 4011–4030 (1990); S. Ikegami et al. *Tetrahedron*, 44, 5333–5342 (1988); W. Oppolzer et al. *Tet. Lets.* 30, 6009–6010 (1989); *Synthesis of Optically Active α-Amino-Acids*, R. M. Williams (Pergamon Press, Oxford 1989); M. J. O'Donnell ed.: *α-Amino-Acid Synthesis*, Tetrahedron Symposia in print, No. 33, *Tetrahedron* 44, No. 17 (1988); U. Schöllkopf, *Pure Appl. Chem.* 55, 1799 (1983); U. Hengartner et al. *J. Org. Chem.*, 44, 3748–3752 (1979); M. J. O'Donnell et al. *Tet. Lets.*, 2641–2644 (1978); M. J. O'Donnell et al. *Tet. Lets.* 23, 4255–4258 (1982); M. J. O'Donnell et al. *J. Am. Chem. Soc.*, 110, 8520–8525 (1988).

The deaminobromination described in Reaction Scheme F.1 can be performed utilizing conditions described in Compagnone, R. S. and Rapoport, H., *J. Org. Chem.*, 51, 1713–1719 (1986); U.S. Pat. No. 5,322,942, issued Jun. 21, 1994; Overberger, C. G. and Cho, I., *J. Org. Chem.*, 33, 3321–3322 (1968); or Pfister, K. et al., *J. Am. Chem. Soc.*, 71, 1096–1100 (1949).

For example, an α-amino carboxylic acid of formula (8) and a suitable bromide, such as hydrogen bromide or potassium bromide in acidic solution, such as sulfuric acid, is treated with sodium nitrite. The reaction temperature is carried out a temperatures of from about –25° C. to about ambient temperature and require about 1 to 5 hours. The product can be isolated and purified by techniques well known in the art, such as acidification, extraction, evaporation, chromatography, and recrystallization to give the compound of formula (3b1) or formula (3b2)in which Y is bromo and A is —OH. The product can be isolated and purified by techniques well known and appreciated in the art, such as acidification, basification, filtration, extraction, evaporation, trituration, chromatography, and recrystallization.

Reaction Scheme F.2

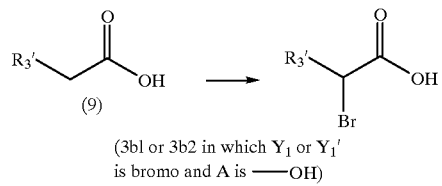

(9)

(3b1 or 3b2 in which $Y_1$ or $Y_1'$ is bromo and A is ——OH)

In Reaction Scheme F.2, an appropriate carboxylic acid of formula (9) is brominated to give compound of formula (3b1) or formula (3b2) in which Y is bromo and A is —OH.

An appropriate carboxylic acid of formula (9), and protected forms thereof, is one which is one in which $R_{3'}$ is $R_3$ as desired in the final product of formula (1) or gives rise after deprotection to $R_3$ as desired in the final product of formula (1). In addition, carboxylic acid of formula (9) may also be one in which the stereochemistry at the $R_{3'}$ bearing carbon gives rise after displacement to the stereochemistry as desired at that carbon in the final product of formula (1).

For example, a mixture of a carboxylic acid of formula (9) and dry red phosphorous are treated dropwise with bromine at temperature ranging from about −20° to about 10° C. The reaction mixture is then warmed to room temperature and then heated to about 80° C. for about 2–5 hours. The reaction mixture is then cooled to room temperature, poured into water containing sodium bisulfite, and neutralized using solid sodium carbonate. The aqueous layer is extracted and acidified with a suitable acid, such as concentrated hydrochloric acid, The precipitate is collected by filtration and dried to give the compound of formula (3b1) or formula (3b2) in which Y is bromo and A is —OH. The product can be isolated and purified by techniques well known and appreciated in the art, such as acidification, basification, filtration, extraction, evaporation, trituration, chromatography, and recrystallization.

Compounds of formula (8) and (9) in which $R_{3'}$ is a —$(CH_2)_m$—W for use in Reaction Schemes F.1 and F.2 are prepared according to Reaction Scheme G.1 and G.2.

Reaction Scheme G.1

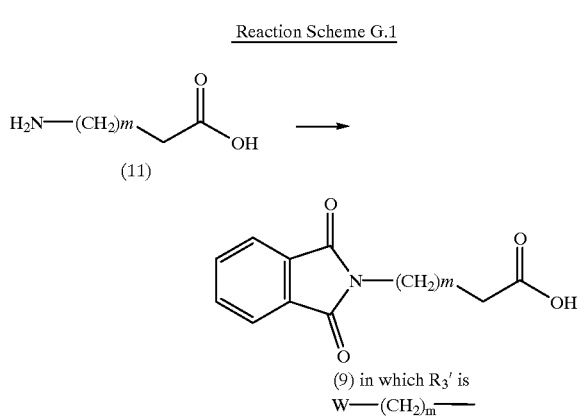

(9) in which $R_{3'}$ is
W—$(CH_2)_m$—

In Reaction Scheme G.1 an appropriate ω-amino carboxylic acid of formula (11) is converted to an compound of formula (9) in which $R_{3'}$ is W—$(CH_2)_m$—. An appropriate ω-amino carboxylic acid of formula (11) is one in which m is as desired in the final product of formula (1) and are readily available in the art. For example, the reaction is carried out in a suitable polar solvent, such as water, ethanol, diethyl ether, tetrahydrofuran, or a water/ethanol solvent mixture using a suitable base, such as sodium carbonate and N-carbethoxyphthalimide. The reaction mixture is typically stirred at about ambient temperature for 1–5 hours. The product can be isolated and purified by techniques well known in the art, such as acidification, extraction, evaporation, chromatography, and recrystallization to give the desired compound of formula (9) in which $R_{3'}$ is W—$(CH_2)_m$—.

Reaction Scheme G.2

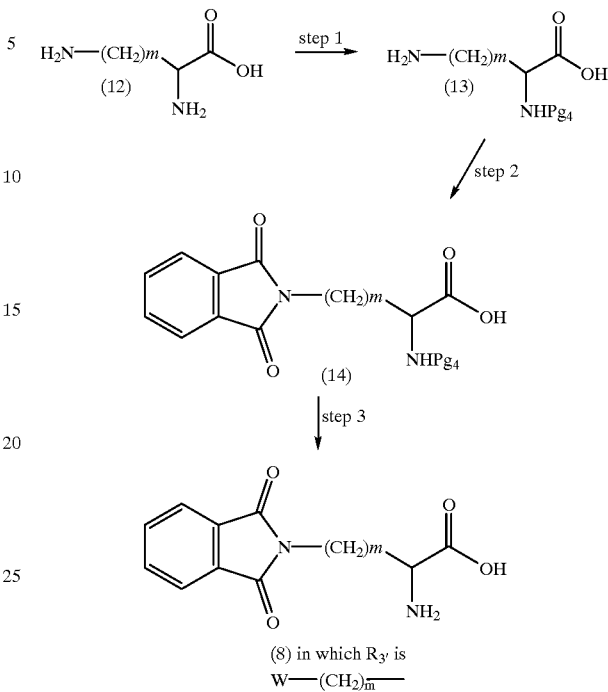

(8) in which $R_{3'}$ is
W—$(CH_2)_m$—

Reaction Scheme G.2, step 1, an appropriate α,ω-diamino acid of formula (12) undergoes a selective N-α-protection to give an N-α-protected-107-diamino acid of formula (13). An appropriate α,ω-diamino acid of formula (12) is one in which m is as desired in the final product of formula (1).

For example, a selective N-α-protection of a suitable α,ω-diamino acid, such as L-lysine (formula 12 in which m is 4), is accomplished by masking the ω-amino group by formation of a benzylidene imine. The benzylidene imine is formed by dissolving L-lysine monohydrochloride in lithium hydroxide and cooling the solution to a temperature ranging from about 0° to 10° C. Freshly distilled benzaldehyde is then added and the solution is shaken. N-ω-benzylidene-L-lysine is recovered by filtration and evaporation. The α-amino group of the N-ω-benzylidene-L-lysine then undergoes protection, such as the introduction of a Cbz or t-Boc group, followed by hydrolytic cleavage of the imine in situ to give N-α-benzyloxy-carbonyl-L-lysine. Accordingly, N-ω-benzylidene-L-lysine is added to a mixture of sodium hydroxide and ethanol, cooled to a temperature of from about −5° to about −25° C. Then, precooled solutions of benzyloxycarbonyl chloride in a solvent, such as ethanol, is added to the reaction mixture. The temperature is maintained in a range of from about −10° to about −25° C. during the course of addition, and may allowed to rise afterwards. The reaction mixture is then acidified using a suitable acid, such as precooled hydrochloric acid, and N-α-benzyloxycarbonyl-L-lysine, which corresponds to formula (13) where m is 4, is recovered by filtration evaporate and recrystallization.

In Reaction Scheme G.2, step 2, N-α-benzyloxycarbonyl-L-lysine or other compounds of formula (13) is converted to ω-phthalimido-α-benzyloxycarbonyl-L-lysine or other ω-phthalimido-α-aminoprotected carboxylic acid of formula (14) by the method described in Reaction Scheme G.1, above.

In Reaction Scheme G.2, step 3, the ω-phthalimido-α-aminoprotected carboxylic acid of formula (14) is deprotected to give compound of formula (8) in which $R_{3'}$ is $W—(CH_2)_m—$.

For example, ω-phthalimido-α-benzyloxycarbonyl-L-lysine is contacted with hydrogen in the presence of a hydrogenation catalyst, such as 10% palladium/carbon. The reactants are typically contacted in a suitable solvent mixture such as ethanol, methanol, water, ethanol/water mixtures, or methanol/water mixtures. The reactants are typically shaken under a hydrogen atmosphere of 35–45 psi at room temperature for a period of time ranging from 5–24 hours. The product is typically recovered by filtration and evaporation of the solvent.

A route for preparing the compounds of formula (3b1) and formula (3b2) in which $Y_1$ is protected thio is presented in Reaction Reaction Scheme H. The reagents and starting materials are readily available to one of ordinary skill in the art. In Reaction Reaction Scheme H all substituents, unless otherwise indicated, are as previously defined.

Reaction Scheme H

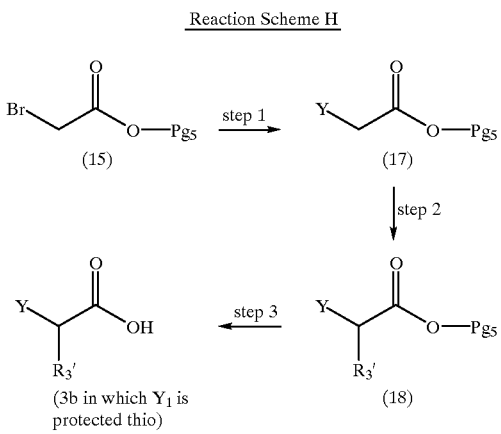

(3b in which $Y_1$ is protected thio)

In Reaction Scheme H, step 1, a bromoacetate of formula (15) is contacted with an appropriate thiol to give a protected acetic acid ester of formula (17). In a bromoacetate of formula (15) $Pg_5$ is a protecting group, such as methyl, ethyl, t-butyl, and benzyl. An appropriate thiol is one which gives rise to a protected thio group, Y, in the product of formula (3b). The use of 4-methoxybenzylmercaptan is preferred.

For example, a bromoacetate of formula (15) is contacted with an appropriate thiol in a suitable organic solvent, such as dimethylformamide. Advantageously, the solvent is degassed. The reaction is carried out using a suitable base, such as sodium hydroxide, triethylamine, or N,N-diisopropylethylamine. The reaction is carried out at temperatures of from about –50° to about ambient temperature and requires about 1 to 72 hours. The protected acetic acid ester of formula (17) can be isolated and purified by methods well known and appreciated in the art, such as extraction, evaporation, chromatography, and distillation, and recrystallization.

In Reaction Reaction Scheme H, step 2, the protected acetic acid ester of formula (17) is alkylated with an appropriate akylating agent to give a compound of formula (18). In Reaction Reaction Scheme H, step 2, an appropriate alkylating agent is one which transfers $R_{3'}$ which is $R_3$ as desired in the final product of formula (1) or gives rise after deprotection to $R_3$ as desired in the final product of formula (1) or gives rise to $R_{3''}$ as defined in Reaction Scheme D, step 1. Appropriate alkylating agents include alkylhalides, such as methyl iodide, methyl bromide, ethyl bromide, propyl bromide, propyl chloride, butyl bromide, butyl chloride, and the like; benzyl bromide, benzyl chloride, substituted benzyl bromide, substituted benzyl chloride, ethyl bromoacetate, t-butyl bromoaceate, ethyl 3-chloropropionate, ethyl 3-bromopropionate, ethyl 5-bromovalerate, ethyl 4-bromobutyrate, 3-chloropropionamide, 2-bromoethylbenzene, substituted 2-bromoethylbenzene, 1-chloro-3-phenylpropane, 1-bromo-4-phenylbutane, and the like, N-(2-bromoethyl)phthalimide, N-(3-bromopropyl) phthalimide, N-(4-bromobutyl)phthalimide, and the like; 1-bromo-2-phenylethane, 1-bromo-3-phenylpropane, 1-bromo-4phenylbutane, and the like.

For example, a protected acetic acid ester of formula (17) is alkylated with an appropriate alkylating agent. The reaction is carried out in a suitable solvent, such as diethyl ether) tetrahydrofuran, dimethylformamide, and toluene using a suitable base, such as sodium hydride, potassium hydride, potassium t-butoxide, lithium bis(trimethylsilyl)amide, sodium bis(trimethylsilyl)amide, potassium bis (trimethylsilyl)amide, or lithium diisopropylamide. The reaction is generally carried out at temperatures of about –70° C. to about room temperature and require from about 1–24 hours. The product can be isolated by techniques well known in the art, such as extraction, evaporation, and precipitation and can be purified by chromatography and recrystallization.

In Reaction Scheme H, step 3, the compound of formula (18) the carboxy protecting group $Pg_5$ is selectively removed to give a compound of formula (3b) in which Y is protected thio. Such deprotection of esters to acids in the presence of suitable thio protecting groups are well known and appreciated in the art.

The following examples present typical syntheses of the compounds of formula (1). These examples are understood to be illustrative only and are not intended to limit the scope of the present invention in any way.

EXAMPLE 1

2-Mercapto-pentanoyl-(L)-homo-phenylalanyl-(L)-phenylalanine

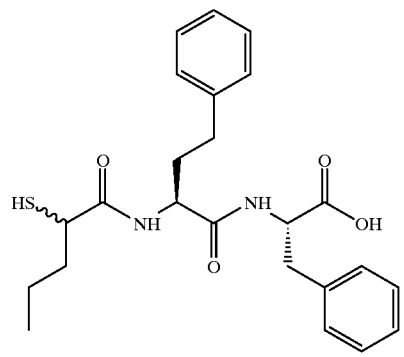

1.1 Synthesis of t-Boc-(L)-homophenylalanine methyl ester

Combine t-Boc-(L)-homophenylalanine (2.80 g, 10.0 mmol), cesium carbonate (1.81 g, 5.56 mmol), and dimethylformamide (15 mL). Add methyl iodide (0.7 mL, 11.2 mmol). After 3 hours, partition the reaction mixture between methyl t-butyl ether and brine, extract the aqueous layer twice with methyl t-butyl ether, dry over $Na_2SO_4$, filter, and evaporate in vacuo to give the title compound: $R_f$=0.67 (silica gel, 1/1 ethyl acetate/hexane).

1.2 Synthesis of (L)-homophenylalanine methyl ester trifluoroacetic acid salt Combine t-Boc-(L)-homophenylalanine methyl ester (2.94 g, 10.0 mmol) and dichloromethane (30 mL). Add trifluoroacetic acid (10 mL). After 2 hours, evaporate in vacuo to obtain a residue. Repeatedly, combine the residue and carbon tetrachloride and evaporate in vacuo to give the title compound.

1.3 Synthesis of 2-bromopentanoyl-(L)-homophenylalanine methyl ester

Combine (L)-homophenylalanine methyl ester trifluoroacetic acid salt (3.6 g, 10 mmol), N-methylmorpholine (3.3 mL, 30 mmol), and dichloromethane (20 mL). Add 2-bromovaleric acid (2.0 mL, 15.3 mmol), hydroxybenzotriazole (2.07 g, 15.3 mmol), and 1-(3-dimethylaminopropyl)-3-ethylcarbodiimide hydrochloride (2.93 g, 15.3 mmol). After 1 hour, partition the reaction mixture between methyl t-butyl ether and an aqueous 5% sulfuric acid solution. Separate the layers, extract the organic layer with a saturated sodium bicarbonate solution and then brine. Dry over $Na_2SO_4$, filter, and evaporate in vacuo to give a residue. Chromatograph the residue on silica gel eluting sequentially with 3/1 hexane/ethyl acetate and then 2.5/1 hexane/ethyl acetate to give the title compound: $R_f$=0.55 (silica gel, 1/1 ethyl acetate/hexane).

1.4 Synthesis of 2-(4-methoxybenzylthio)-pentanoyl-(L)-homophenylalanine methyl ester Combine 2-bromopentanoyl-(L)-homophenylalanine methyl ester (3.6 g, 10 mmol), 4-methyoxybenzylmercaptan (3.48 mL, 25 mmol), and tetrabutylammonium iodide (about 50 mg) in dimethylformamide (10 mL). Degas by repeatedly applying vacuum and filling the vessel with nitrogen. Add cesium carbonate (4.10 g, 12.5 mmol). After 15 hours, partition the reaction mixture between water and methyl t-butyl ether, saturate the aqueous layer with sodium chloride. Extract the aqueous layer with brine, dry over $Na_2SO_4$, filter, and evaporate in vacuo to give a residue. Chromatograph the residue on silica gel eluting sequentially with 4/1 hexane/ethyl acetate and then 2.5/1 hexane/ethyl acetate to give the title compound: $R_f$=0.44 (silica gel, 2.5/1 hexane/ethyl acetate).

1.5 Synthesis of 2-(4-methoxybenzylthio)-pentanoyl-(L)-homophenylalanine

Combine 2-(4-methoxybenzylthio)-pentanoyl-(L)-homophenylalanine methyl ester (3.50 g, 8.15 mmol) and methanol (30 mL) and tetrahydrofuran (30 mL). Cool in an ice bath. Add an aqueous 2M lithium hydroxide solution (8.2 mL, 16.4 mmol). After 18 hours, adjust the pH to about 6 using an aqueous 10% hydrochloric acid solution and evaporate in vacuo to give a residue. Partition the residue between dichloromethane and water, adjust the pH of the aqueous layer to about 1 using an aqueous 10% hydrochloric acid solution. Separate the layers, extract the aqueous layer repeatedly with ethyl acetate. Combine the organic layers, dry over $Na_2SO_4$, filter, and evaporate in vacuo to give a residue. Chromatograph the residue on silica gel eluting with 95% 1/1 hexane/ethyl acetate/5% acetic acid to give the title compound.

1.6 Synthesis of 2-(4-methoxybenzylthio)-pentanoyl-(L)-homophenylalanyl-(L)-phenylalanine t-butyl ester Combine 2-(4-methoxybenzylthio)-pentanoyl-(L)-homophenylalanine (0.14 g, 0.34 mmol), (L)-phenylalanine t-butyl ester hydrochloride salt (0.174 g, 68 mmol), and 1-(3-dimethylaminopropyl)-3-ethylcarbodiimide hydrochloride (0.13 g, 0.67 mmol) in dichloromethane (5 mL). Add N-methylmorpholine (0.1 mL, 1.01 mmol) and hydroxybenzotriazole (0.091 g, 0.67 mmol). After 3 hours, after 1 hour, partition the reaction mixture between methyl t-butyl ether and an aqueous 5% sulfuric acid solution. Separate the layers, extract the organic layer with a saturated sodium bicarbonate solution and then brine. Dry over $Na_2SO_4$, filter, and evaporate in vacuo to give a residue. Chromatograph the residue on silica gel eluting sequentially with 3/1 hexane/ethyl acetate and then 1/1 hexane/ethyl acetate to give the title compound: $R_f$=0.45 (silica gel, 1/1 ethyl acetate/hexane).

1.7 Synthesis of 2-mercapto-pentanoyl-(L)-homophenylalanyl-(L)-phenylalanine Combine 2-(4-methoxybenzylthio)-pentanoyl-(L)-homophenylalanyl-(L)-phenylalanine t-butyl ester (0.20 g, 0.33 mmol), mercury (II) acetate (0.134 g, 0.42 mmol), and anisole (0.37 mL, 3.4 mmol) in dichloromethane (9 mL). Cool in an ice bath and degas by repeatedly applying vacuum and filling the vessel with nitrogen, Add trifluoroacetic acid (4 mL). After 1 hour, warm to ambient temperature. After 3 hours, purge with hydrogen sulfide (gas) for about 10 minutes. Filter and evaporate in vacuo to give a residue. Repeatedly, combine the residue and carbon tetrachloride and evaporate in vacuo to give a residue. Triturate the residue with hexane to give the title compound as a solid (85 mg, 57%).

EXAMPLE 2

(S)-2-Mercapto-3-methylbutyroyl-(L)-homophenylalanyl-(L)-phenylalanine

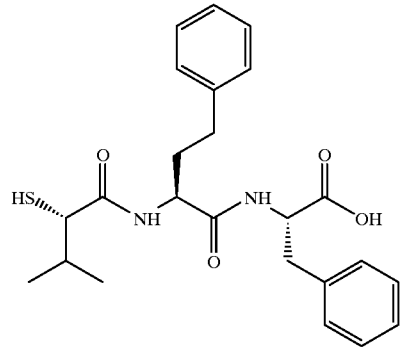

Combine Fmoc-(L)-phenylalanine-NovaSyn® TGT resin (1.0 g, 0.15 mmol/g, Nova Biochem), dimethylformamide (3 mL) and 50% piperidine/dimethylformamide (3 mL). After 5 minutes, filter, add dimethylformamide (3 mL) and 50% piperidine/dimethylformamide (3 mL), bubble for 10 minutes, and filter. Rinse the resin with dimethylformamide (10 times 5 mL), dichloromethane (3 times 5 mL), and then dimethylformamide (5 mL). Kaiser (ninhydrin) test indicates complete deprotection. Add Fmoc-(L)-homophenylalanine (0.240 g, 0.5 mmol), O-(7-azabenzotriazol-1-yl)-1,1,3,3-tetramethyluronium hexafluorophosphate (0.228 g, 0.60 mmol), and N,N-diisopropylethylamine (0.21 mL, 1.20 mmol), and dimethylformamide (5 mL). After 15 hours, filter, rinse the resin with dimethylformamide (9 times 5 mL), dichloromethane (3 times 5 mL), and then dimethylformamide (5 mL). Add dimethylformamide (3 mL) and 50% piperidine/ dimethylformamide (3 mL), bubble for 10 minutes, and filter. Rinse the resin with dimethylformamide (10 times 5 mL), dichloromethane (3 times 5 mL), and then dimethylformamide (5 mL). Kaiser (ninhydrin) test indicates complete deprotection. Add (R)-2-bromo-3-methylbutyric acid (0.145 g, 0.6 mmol), 1,3-diisopropylcarbodiimide (0.076 g, 0.60 mmol), and N,N-diisopropylethylamine (0.21 mL, 1.20 mmol) in N-methylpyrrolidinone (5 mL). After 15 hours, filter, rinse the resin with dimethylformamide (9 times 5 mL), dichloromethane (3 times 5 mL), and then dimethylformamide (5 mL). Combine the resin with a degassed solution of potassium thioacetate (0.137 g, 1.2 mmol) in N-methylpyrolidinone (5 mL). After 3 hours, filter and rinse the resin with dimethylformamide (9 times 5 mL). Combine the resin with a degassed saturated methanolic ammonia solution (5 mL). After 5 minutes, filter and rinse the resin with methanol (5 times 5 mL). Combine the resin and a degassed 95% trifluoroacetic acid/4% water/1% 2-mercaptoethanol solution (10 mL). After 3 hours, filter, rinse with 50% trifluoroacetic acid/dichloromethane (2 times 10 mL). Concentrate the filtrate in vacuo to give a residue. Combine the residue with 1% trifluoroacetic acid/ acetonitrile solution and evaporate under a stream of nitrogen to give a residue. Combine the residue and water (about 4 mL) and lyophilize to give a residue. Combine the residue and acetonitrile and water and again lyophilize to give a residue. Purify by HPLC to give the title compound: retention time=4:24 minutes, YMC Inc. 4.0 mm×50 mm ODS-A column, flow rate 1.0 mL/minute, initial conditions 70% A (95% water/5% acetonitrile/0.1% trifluoroacetic acid) and 30% B (5% water/95% acetonitrile/0.085% trifluoracetic acid) and a linear gradient over 5 minutes to 100% B. Mass Spectrum (MH$^+$=443).

EXAMPLE 3

(S)-2-Mercapto-3-methylbutyroyl-(L)-leucyl-(L)-phenylalanine

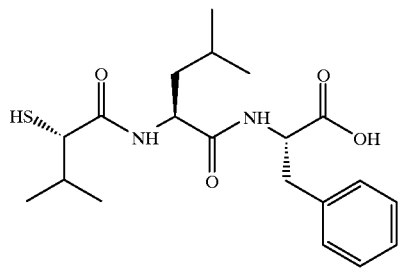

Prepare by the method of Example 2 using Fmoc-(L)-leucine (0.212 g, 0.5 mmol) to give after purification by HPLC the title compound: retention time=3:57 minutes, YMC Inc. 4.0 mm×50 mm ODS-A column, flow rate 1.0 mL/minute, initial conditions 70% A (95% water/5% acetonitrile/0.1% trifluoroacetic acid) and 30% B (5% water/95% acetonitrile/0.085% trifluoracetic acid) and a linear gradient over 5 minutes to 100% B. Mass Spectrum (MH$^+$=395).

EXAMPLE 4

(S)-2-Mercapto-3-methylbutyroyl-(L)-methionyl-(L)-phenylalanine

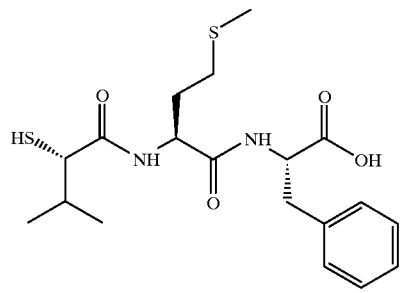

Prepare by the method of Example 2 using Fmoc-(L)-methionine (0.212 g, 0.5 mmol) to give after purification by HPLC the title compound: retention time=3:34 minutes, YMC Inc. 4.0 mm×50 mm ODS-A column, flow rate 1.0 mL/minute, initial conditions 70% A (95% water/5% acetonitrile/0.1% trifluoroacetic acid) and 30% B (5% water/95% acetonitrile/0.085% trifluoracetic acid) and a linear gradient over 5 minutes to 100% B. Mass Spectrum (MH$^+$=413).

EXAMPLE 5

(S)-2-Mercapto-3-methylbutyroyl-(L)-lysyl-(L)-phenylalanine trifluoroacetic acid salt

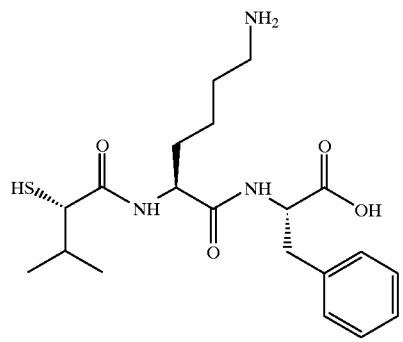

Prepare by the method of Example 2 using α-Fmoc-ω-t-Boc-(L)-leucine (0.281 g, 0.5 mmol) to give after purification by HPLC the title compound:retention time=1:19 minutes, YMC Inc. 4.0 mm×50 mm ODS-A column, flow rate 1.0 mL/minute, initial conditions 70% A (950/0 water/5% acetonitrile/0.1% trifluoroacetic acid) and 30% B (5% water/95% acetonitrile/0.085% trifluoracetic acid) and a linear gradient over 5 minutes to 100% B. Mass Spectrum (MH$^+$=410).

EXAMPLE 6

(S)-2-Mercaptopentanoyl-(L)-homo-phenylalanyl-(L)-phenylalanine N-methyl amide

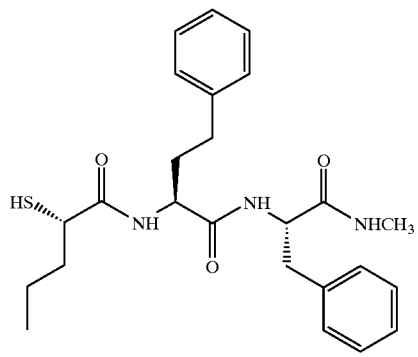

6.1 Synthesis of t-Boc-(L)-phenylalanine-N-methyl amide

Combine t-Boc-(L)-phenylalanine (8.00 g, 30.2 mmol) and tetrahydrofuran (20 mL). Cool to about −30° C. and add sequentially N-methylmorpholine (3.5 mL, 32 mmol) and then isobutyl chloroformate (4.5 mL, 35 mmol). After 10 minutes, add 40% aqueous methylamine (13 mL, 380 mmol). After 2 hours, concentrate the reaction mixture in vacuo, combine the evaporated reaction mixture and dichloromethane (125 mL) and extract with an aqueous 1M hydrochloric acid solution and then a saturated aqueous sodium bicarbonate solution. Dry the organic layer over $Na_2SO_4$, filter, and evaporate in vacuo to give the title compound, which is used without further purification.

6.2 Synthesis of (L)-phenylalanine-N-methyl amide trifluoroacetic acid salt Combine t-Boc-(L)-phenylalanine-N-methyl amide (8.4 g, 30 mmol), methylene chloride (100 mL), and trifluoroacetic acid (20 mL). After 3 hours, evaporate in vacuo to give a residue. Repeatedly, combine the residue and carbon tetrachloride and toluene and evaporate in vacuo to give a residue. Triturate the residue with diethyl ether to yield the title compound as a white solid (9.12 g, 100%).

6.3 Synthesis of 2-(4-methoxybenzylthio)-pentanoyl-(L)-homophenylalanyl-(L)-phenylalanine N-methyl amide Combine (L)-phenylalanine N-methyl amide trifluoroacetic acid salt (0.22 g, 0.75 mmol) and N-methylmorpholine (0.09 mL, 0.83 mmol) in dichloromethane (5 mL). After 15 minutes, add 2-(4-methoxybenzylthio)-pentanoyl-(L)-homophenylalanine (0.18 g, 0.45 mmol) and 1-(3-dimethylaminopropyl)-3-ethylcarbodiimide hydrochloride (0.086 g, 0.45 mmol) and hydroxybenzotriazole (0.060 g, 0.45 mmol). After 18 hours, partition the reaction mixture between ethyl acetate and an aqueous 5% sulfuric acid solution. Separate the layers, extract the organic layer with a saturated sodium bicarbonate solution and then brine. Dry over $Na_2SO_4$, filter, and evaporate in vacuo to give a residue. Chromatograph the residue on silica gel eluting with 4% methanol/dichloromethane to give the title compound.

6.4 Synthesis of 2-mercapto-pentanoyl-(L)-homophenylalanyl-(L)-phenylalanine-N-methyl amide Combine 2-(4-methoxybenzylthio)-pentanoyl-(L)-homophenylalanyl-(L)-phenylalanine N-methyl amide (0.26 g, 0.45 mmol), mercury (II) acetate (0.156 g, 0.49 mmol), and anisole (0.49 mL, 4.5 mmol) in dichloromethane (10 mL). Cool in an ice bath and degas by repeatedly applying vacuum and filling the vessel with nitrogen. Add trifluoroacetic acid (2 mL). After 3 hours, filter and evaporate in vacuo to give a residue. Repeatedly, combine the residue and carbon tetrachloride and evaporate in vacuo to give a residue. Triturate the residue with hexane to give the title compound as a solid (165 mg, 80.4%).

EXAMPLE 7

(S)-2-Mercapto-3-methylbutyroyl-(L)-homo-phenylalanyl-(L)-phenylalanine N-methyl amide

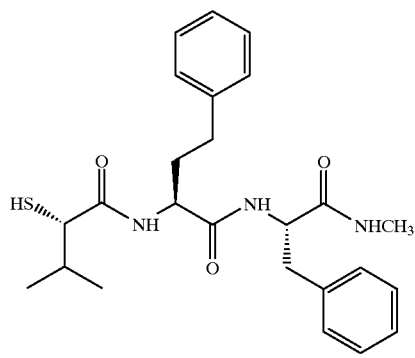

7.1 Synthesis of t-Boc-(L)-homophenylalanyl-(L)-phenylalanine N-methyl amide Combine t-Boc-(L)-homopenylalanine (1.37 g, 4.90 mmol) and (L)-phenylalanine N-methyl amide trifluoroacetic acid salt (1.43 g, 4.90 mmol), Combine (L)-homophenylalanine methyl ester trifluoroacetic acid salt (3.6 g, 10 mmol), N-methylmorpholine (0.48 mL, 4.90 mmol), and hydroxybenzotriazole (0.663 g, 4.90 mmol) in dichloromethane (20 mL). Add 1-(3-dimethylaminopropyl)-3-ethylcarbodiimide hydrochloride (1.13 g, 5.8 mmol). After 18 hour, dilute the reaction mixture with dichloromethane. Extract with an aqueous 5% sulfuric acid solution, a saturated sodium bicarbonate solution, and then brine. Dry the organic layer over $Na_2SO_4$, filter, and evaporate in vacuo to give the title compound.

7.2 Synthesis of (L)-homophenylalanyl-(L)-phenylalanine N-methyl amide trifluoroacetic acid salt Combine t-Boc-(L)-homophenylalanyl-(L)-phenylalanine N-methyl amide (5.0 mmol) and dichloromethane (15 mL). Add trifluoroacetic acid (5 mL). After 2 hours, evaporate in vacuo to obtain a residue. Repeatedly, combine the residue and carbon tetrachloride and evaporate in vacuo to give the title compound.

7.3 Synthesis of (R)-2bromo-3-methylbutyroyl-(L)-homophenylalanyl-(L)-phenylalanine N-methyl amide Combine (L)-homophenylalanyl-(L)-phenylalanine N-methyl amide trifluoroacetic acid salt (0.453 g, 1.0 mmol) and (R)-bromo-3-methylbutyric acid (0.181 g, 1.00 mmol), N-methylmorpholine (0.11 mL, 1.0 mmol), and hydroxybenzotriazole (0.135 g, 1.0 mmol) in dichloromethane (10 mL). Add 1-(3-dimethylaminopropyl)-3-ethylcarbodiimide hydrochloride (0.23 g, 1.0 mmol). After 18 hour, dilute the reaction mixture with ethyl acetate and an aqueous 5% sulfuric acid solution to form a precipitate. Filter, rinse with water and ethyl acetate. Separate the filtrate and extract the organic layer with a saturated sodium bicarbonate solution and then brine. Dry the organic layer over $Na_2SO_4$, filter, and evaporate in vacuo to give a residue. Combine the precipitate and the residue to give the title compound 0.466 g, 93%).

7.4 Synthesis of (S)-2-thioacetyl-3-methylbutyroyl-(L)-homophenylalanyl-(L)-phenylalanine N-methyl amide Combine (R)-2-bromo-3-methylbutyroyl-(L)-homophenylalanyl-(L)-phenylalanine N-methyl amide (0.466 g, 0.93 mmol) and dimethylformamide (3 mL). Add thioacetic acid (0.066 mL, 0.93 mmol) and cesium carbonate (0.151 g, 0.46 mmol). After 18 hours, partition the reaction mixture between ethyl acetate and an aqueous 2 M hydrochloric acid solution. separate the layers, extract the organic layer with water and a saturated aqueous sodium bicarbonate solution, dry over $Na_2SO_4$, filter, and evaporate in vacuo to give a residue. Chromatograph the residue on silica gel eluting sequentially with 10% acetone/dichloromethane, 15% acetone/dichloromethane, and then 20% acetone/dichloromethane to give the title compound.

7.5 Synthesis of (S)-2-mercapto-3-methylbutyroyl-(L)-homophenylalanyl-(L)-phenylalanine N-methyl amide Combine (S)-2-thioacetyl-3-methylbutyroyl-(L)-homophenylalanyl-(L)-phenylalanine N-methyl amide ((0.10 g, 0.20 mmol) and deoxegenated methanol (5 mL). Add an aqueous solution of lithium hydroxide (0.3 mL, 1 M, 0.3 mmol). After 15 minutes, add water and an aqueous 2M hydrochloric acid solution to give a solid. Collect the solid by filtration, rinse with water and dry to give the title compound.

In a further embodiment, the present invention provides a method of inhibiting matrix metalloproteinase (MMP) to a patient in need thereof comprising administering to the patient an effective matrix metalloproteinase inhibiting amount of a compound of formula (1).

As used herein, the term "patient" refers to warm-blooded animals or mammals, including guinea pigs, dogs, cats, rats, mice, hamsters, rabbits and primates, including humans. A patient is in need of treatment to inhibit MMP when it would be beneficial to the patient to reduce the physiological effect of active MMP. For example, a patient is in need of treatment to inhibit MMP when a patient is suffering from a disease state characterized by excessive tissue disruption or tissue degradation, such as, but not limited to, a neoplastic disease state or cancer; rheumatoid arthritis; osteoarthritis; cardiovascular disorders, such as atherosclerosis; corneal ulceration; dental diseases, such as gingivitis or periodontal disease; and neurological disorders, such as multiple sclerosis; chronic inflammatory disorders, such as emphysema and especially smoking-induced emphysema.

The identification of those patients who are in need of treatment to inhibit MMP is well within the ability and knowledge of one skilled in the art. A clinician skilled in the art can readily identify, by the use of clinical tests, physical examination and medical/family history, those patients who are suffering from disease states characterized by excessive tissue disruption or tissue degradation.

An "effective matrix metalloproteinase inhibiting amount" of a compound of formula (1) is an amount which is effective, upon single or multiple doge administration to the patient, in providing relief of symptoms associated with MMP and is thus effective in inhibiting MMP-induced tissue disruption and/or MMP-induced tissue degradation. As used herein, "relief of symptoms" of MMP-mediated conditions refers to decrease in severity over that expected in the absence of treatment and does not necessarily indicate a total elimination or cure of the disease. Relief of symptoms is also intended to include prophylaxis.

An effective matrix metalloproteinase inhibiting dose can be readily determined by the use of conventional techniques and by observing results obtained under analogous circumstances. In determining the effective dose, a number of factors are considered including, but not limited to: the species of the patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

An effective matrix metalloproteinase inhibiting amount of a compound of formula (1) will generally vary from about 0.1 milligram per kilogram of body weight per day (mg/kg/day) to about 300 milligrams per kilogram of body weight per day (mg/kg/day). A daily dose of from about 1 mg/kg to about 100 mg/kg is preferred.

A neoplastic disease state refers to an abnormal state or condition characterized by rapidly proliferating cell growth or neoplasm. Neoplastic disease states for which treatment with a compound of formula (1) will be particularly useful include: Leukemias, such as, but not limited to, acute lymphoblastic, chronic lymphocytic, acute myeloblastic and chronic myelocytic; Carcinomas and adenocarcinomas, such as, but not limited to, those of the cervix, oesophagus, stomach, small intestines, colon, lungs (both small and large cell), breast and prostate; Sarcomas, such as, but not limited to, oesteroma, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, follicullar reticulum, cell sarcoma and Hodgkin's Disease. Neoplastic disease states for which treatment with a compound of formula (1) will be particularly preferred include carcinomas and adenocarcinomas, particularly of the breast, prostate and lung.

Atherosclerosis is a disease state characterized by the development and growth of atherosclerotic lesions or plaque. The identification of those patients who are in need of treatment for atherosclerosis is well within the ability and knowledge of one of ordinary skill in the art. For example, individuals who are either suffering from clinically significant atherosclerosis or who are at risk of developing clinically significant atherosclerosis are patients in need of treatment for atherosclerosis. A clinician of ordinary skill in the art can readily determine, by the use of clinical tests, physical examination and medical/family history, if an individual is a patient in need of treatment for atherosclerosis.

The term "chronic inflammatory disease" refers to diseases or conditions characterized by persistent inflammation in the absence of an identifiable irritant or microbial pathogen. Inflammatory diseases for which treatment with a compound of formula (1) will be particularly useful include: emphysema, chronic bronchitis, asthma, and chronic inflammation, and especially smoking-induced emphysema.

In effecting treatment of a patient, a compound of formula (1) can be administered in any form or mode which makes the compound bioavailable in effective amounts, including oral and parenteral routes. For example, the compound can be administered orally, subcutaneously, intramuscularly, intravenously, transdermally, topically, intranasally, rectally, inhalation, and the like. Oral and inhalation administration is generally preferred. One skilled in the art of preparing formulations can readily select the proper form and mode of administration depending upon the disease state to be treated, the stage of the disease, and other relevant circumstances. *Remington's Pharmaceutical Sciences,* 18th Edition, Mack Publishing Co. (1990).

A compound of formula (1) can be administered in the form of pharmaceutical compositions or medicaments which are made by combining a compound of formula (1) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, gels, ointments, aerosol or the like.

The pharmaceutical compositions may be administered orally, for example, with an inert diluent or with an edible carrier. They may be enclosed in gelatin capsules or compressed into tablets. For the purpose of oral therapeutic administration, a compound of formula (1) may be incorporated with excipients and used in the form of tablets, troches, capsules, elixirs, suspensions, syrups, wafers, chewing gums and the like. These preparations should contain at least 4% of a compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1% and about 50% of the weight thereof. The amount of the active ingredient present in such compositions is such that a suitable dosage will be obtained. Preferred compositions and preparations are able to be determined by one skilled in the art.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

The compounds of the present invention may also be administered by inhalation, such as by aerosol or dry powder. Delivery may be by a liquefied or compressed gas or a suitable pump system which dispenses the compounds of the present invention or a formulation thereof. Formulations for administration by inhalation of compounds of formula (1) may be delivered in single phase, bi-phasic, or tri-phasic systems. A variety of systems are available for the administration by aerosol of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontainers, and the like. Preferred aerosol and dry powder formulations for administration by inhalation can be determined by one skilled in the am.

The selective MMP-12 inhibitors of the present invention can be evaluated by the procedures that follow.

Example A

Source and Activation of proMMP-1

ProMMP-1 (EC3.4.24.7; interstitial collagenase) was purified from culture medium of human rheumatoid synovial fibroblasts stimulated with macrophage-conditioned medium according to Okada, Y. et al., *J. Biol. Chem.* 261, 14245–14255 (1986). The active MMP-1 was obtained by treatment of proMMP-1 with trypsin (5 $\mu$g/mL) at 37° C. for 30 minutes, followed by addition of soybean trypsin inhibitor (50 $\mu$g/mL).

Determination of Inhibition Constant ($K_i$) for MMP-1

The activated MMP-1 is assayed using a fluorogenic substrate, Mca-Pro-Leu-Gly-Leu-Dpa-Ala-Arg-NH$_2$, Knight, C. G. et al., *FEBS Lett.* 296, 263–266 (1992), at 37° C. in 2.0 mL of assay buffer containing 50 mM Tris, pH 7.6, 0.2 M sodium chloride, 50 mM calcium chloride, and 0.02% Brij-35. The increase in fluorescence due to cleavage of Gly-Leu peptide bond by MMP-3 was monitored with Perkin-Elmer LS50B Fluorimeter ($\lambda_{ex}$ 328 nm, $\lambda_{em}$ 393 nm, excitation slit 2.5, emission slit 10). Substrate and inhibitor stock solutions were made in DMF. For determination of $K_i$ values for MMP-1 inhibitors, a series of intermediate inhibitor solutions were prepared in DMF and 1 or 2 $\mu$L of the diluted inhibitor solution was mixed with 1 $\mu$L of 2 mM substrate solution in DMF in a quartz cuvette containing 2 mL of assay buffer. The enzyme (10 $\mu$L of 0.2 $\mu$M MMP-3 dilution in assay buffer) was added at the last to start the reaction. For routine measurement of a $K_i$ value for a reversible, competitive inhibitor, the initial rates in the presence of at least four inhibitor concentrations (two concentrations above $K_i$ and two concentrations below $K_i$) were measured using [S]=1 µM (<<Km) and [MMP-1]=0.8 nM. Under these conditions, the measured $K_{i,\ app}$ is close to true $K_i$.

Calculation of $K_i$ Values

The $K_i$ for a competitive inhibitor is calculated using: $v_0/v_i=(1+[I]/K_{i,\ app})$ and $K_i=K_{i,\ app}/(1+[S]/K_m)$, where $v_0$ is the initial rate in the absence of inhibitor, $v_i$ is the initial rate in the presence of inhibitor at the concentration of [I], [S] is the substrate concentration, and $K_m$ is the Michaelis constant. If slow binding is observed (i.e. if the approach to the binding equilibrium is slow), the final steady-state rate rather than the initial rate is taken as $v_i$.

Example B

Source and Activation of proMMP-2

Recombinant MMP-2 was purified from the fermentation broth of yeast *Pichia pastoris* that carries the integrated MMP-2 gene into its chromosome. In brief, the full-length cDNA for MMP-2 was obtained by reverse transcription of RNA from human melanoma A375M cell line by the reverse transcriptase polymerase chain reaction (RT-PCR) using sequence specific oligonucleotides. The nucleotide sequence was confirmed by Taq cycle sequencing. The cDNA was ligated into the *Pichia pastoris* expression vector pHIL-D2 in such a way that the expression of pro-MMP-2 is under the control of the methanol inducible alcohol oxidase promoter. The expression construct was digested with either SalI or NsiI and used to transform the *Pichia pastoris* strains KM71 and SMD1168. A large-scale culture of a selected clone designated 24S was performed in a high cell density fermentor and the recombinant MMP-2 was purified from the culture supernatant by gelatin-sepharose 4B (Pharmacia). The enzyme is sufficiently pure at this stage for routine measurement of inhibition. If desired, however, the enzyme may be further purified by AcA 44 gel filtration (Spectra).

Determination of Inhibition Constant ($K_i$) for MMP-2

The active MMP-2 was obtained by activation of proMMP-2 at 37° C. for 1 h with 4-aminophenylmercuric acetate which was then removed by a Sephadex G-50 spin column. The enzyme is assayed using a fluorogenic substrate, Mca-Pro-Leu-Gly-Leu-Dpa-Ala-Arg-NH$_2$, at 37° C. in 2.0 mL of assay buffer containing 50 mM Tris, pH 7.6, 0.2 M sodium chloride, 50 mM calcium chloride, 0.02% Brij-35, and 50 µM β-mercaptoethanol. The increase in fluorescence is monitored ($\lambda_{ex}$ 328 nm, $\lambda_{em}$ 393 nm). Substrate and inhibitor stock solutions are made in DMF. The enzyme is added at the last to start the reaction. For routine measurement of a $K_i$ value for a reversible, competitive inhibitor, the initial rates in the presence of at least four inhibitor concentrations (two inhibitor concentrations above $K_i$ and two below $K_i$) are measured using [S]=1 µM (<<Km) and [MMP-2]=0.4 nM. Under these conditions, the measured $K_{i,\ app}$ is close to true $K_i$.

Example C

Source and Activation of proMMP-3

ProMMP-3 (EC3.4.24.17; Stromelysin-1) was purified from culture medium of human rheumatoid synovial fibroblasts stimulated with macrophage-conditioned medium according to Okada, Y. et al., *J. Biol. Chem.* 261, 14245–14255 (1986). The active MMP-3 was obtained by treatment of proMMP-3 with trypsin (5 µg/mL) at 37° C. for 30 minutes, followed by addition of soybean trypsin inhibitor (50 µg/mL). Aliquots of the activated MMP-3 were stored at −20° C.

Determination of Inhibition Constant ($K_i$) for MMP-3

The activated MMP-3 is assayed using a fluorogenic substrate, Mca-Pro-Leu-Gly-Leu-Dpa-Ala-Arg-NH$_2$, Knight, C. G. et al., *FEBS Lett.* 296, 263–266 (1992), at 37° C. in an assay buffer containing 50 mM Tris, pH 7.6, 0.2 M sodium chloride, 50 mM calcium chloride, and 0.02% Brij-35. The increase in fluorescence due to cleavage of Gly-Leu peptide bond by MMP-3 was monitored with Perkin-Elmer LS50B Fluorimeter ($\lambda_{ex}$ 328 nm, $\lambda_{em}$ 393 nm, excitation slit 2.5, emission slit 10). Substrate and inhibitor stock solutions were made in DMF and 0.1% HCl-DMF, respectively. For determination of $K_i$ values for MMP-3 inhibitors, a series of intermediate inhibitor solutions were prepared in 0.1% HCl-DMF and 1 or 2 µL of the diluted inhibitor solution was mixed with 1 µL of 2 mM substrate solution in DMF in a quartz cuvette containing 2 mL of assay buffer. The enzyme (10 µL of 0.2 µM MMP-3 dilution in assay buffer) was added at the last to start the reaction. For routine measurement of a $K_i$ value for a reversible, competitive inhibitor, the initial rates in the presence of at least four inhibitor concentrations (two concentrations above $K_i$ and two concentrations below $K_i$) were measured using [S]=1 µM (<<Km) and [MMP-3]=1 nM. Under these conditions, the measured $K_{i,\ app}$ is close to true $K_i$.

Calculation of $K_i$ Values

The $K_i$ for a competitive inhibitor is calculated using: $v_0/v_i=(1+[I]/K_{i,\ app})$ and $K_i=K_{i,\ app}/(1+[S]/K_m)$, where $v_0$ is the initial rate in the absence of inhibitor, $v_i$ is the initial rate in the presence of inhibitor at the concentration of [I], [S] is the substrate concentration, and $K_m$ is the Michaelis constant. If slow binding is observed (i.e. if the approach to the binding equilibrium is slow), the final steady-state rate rather than the initial rate is taken as $v_i$.

Example D

Source of MMP-12 (Macrophage Metalloelastase)

MMP-12 (EC3.4.24.65) was cloned, expressed and purified according to Shapiro, S. D. et al., *J Biol. Chem.* 268, 23824–23829 (1993). Autoactivation resulted in the fully processed active form of the enzyme. Aliquots of MMP-12 were stored at −70° C.

Determination of the Inhibition Constant ($K_i$) for MMP-12

The potency of inhibitors of MMP-12 was measured using either quartz cuvettes or microtiter plates. The activity of MMP-12 was measured using a fluorogenic substrate, Mca-Pro-Leu-Gly-Leu-Dpa-Ala-Arg-NH$_2$ SEQ ID NO1, Knight, C. G. et al., *FEBS Lett.* 296,263–266 (1992), at 25° C. in an assay buffer containing 50 mM Tris, pH 7.6, 0.2 M sodium chloride, 50 mM calcium chloride, and 0.02% Brij-35. The increase in fluorescence due to cleavage of Gly-Leu peptide bond by MMP-12 was monitored with a Perkin-Elmer LS50B Fluorimeter ($\lambda_{ex}$ 328 nm, $\lambda_{em}$ 393 nm, excitation slit 2.5, emission slit 10) for the cuvette assay and with a Molecular Devices Fmax fluorescence plate reader ($\lambda_{ex}$ 320 nm, $\lambda_{em}$ 405 nm) for the microtiter plate assay. Substrate and inhibitor stock solutions were made in N,N-dimethylformamide (DMF) and 0.1% HCl-DMF, respectively.

$K_i$ values were determined using the cuvette method by preparing a series of intermediate inhibitors solutions in 0.1% HCl-DMF and mixing the inhibitor with substrate (final concentration 2 µM) in a quartz cuvette containing 2 ml of assay buffer. MMP-12 was added to start the reaction at a concentration of 2 nM and progress curves were generated. For routine measurement of a $K_i$ value for a reversible competitive inhibitor, the initial rates in the presence of at least four inhibitor concentrations (two concentrations above and two concentrations below the $K_i$) were measured [S]=2 µM (<<$K_m$) and [MMP-12]=2 nM. Under these conditions, the measured $K_{i,app}$ is close to the true $K_i$.

$K_i$ values were determined using the microtiter plate method in a manner similar to that described for the cuvette method with some modifications. Four different inhibitor concentrations (50 µl in assay buffer) of each compound were added to separate wells of a microtiter plate and substrate was added (100 µl) to get a final concentration of 4 mM. MMP-12 was added to a final concentration of 2 nM (50 µl) to start the reaction. Cleavage of substrate was recorded every 30 seconds for 30 minutes and progress curves were generated.

Calculation of $K_i$ Values

The $K_i$ for a competitive inhibitor was calculated using: $V_0/V_i=(1+[I]/K_{i,app})$ and $K_i=K_{i,app}/(1+[S]/K_m)$, where $V_0$ is the initial rate in the absence of inhibitor, $V_i$ is the initial rate in the presence of inhibitor at the concentration of [I], [S] is the substrate concentration, and $K_m$ is the Michaelis constant. If slow binding is observed (i.e. if the approach to the binding equilibrium is slow), the final steady-state rate rather than the initial rate is taken as $V_i$.

$K_i$ values showing inhibition of MMP-12 for representative compounds of the present invention are found in Table 1. The MMP-12 values in Table 1 were determined by the method of present Example D.

TABLE 1

| Compound (Example Number) | MMP-1 $K_i$ (nM) | MMP-2 $K_i$ (nM) | MMP-3 $K_i$ (nM) | MMP-12 $K_i$ (nM) |
|---|---|---|---|---|
| Example 1 | 5800 | 1800 | 750 | 13 |
| Example 2 | 5109 | 731 | 365 | 4 |
| Example 3 | 518 | 784 | 1406 | 14 |

TABLE 1-continued

| Compound (Example Number) | MMP-1 K$_i$ (nM) | MMP-2 K$_i$ (nM) | MMP-3 K$_i$ (nM) | MMP-12 K$_i$ (nM) |
|---|---|---|---|---|
| Example 4 | 153 | 798 | 449 | 14 |
| Example 5 | 3913 | 1743 | 1552 | 151 |

Comparative K$_i$ values in Table 2 are presented for the compounds of Examples 1 and 6 and the compounds of Examples 2 and 7. These K$_i$ values demonstrate that the compounds of formula (1) are selective for MMP-12 over MMP-1, MMP-2, and MMP-3 compared to their N-methylamide derivatives. The MMP-1, MMP-2, MMP-3, and MMP-12 values in Table 2 were determined by the method of present Examples A, B, C, and D, respectively.

TABLE 2

| Compound (Example Number) | MMP-1 K$_i$ (nM) | MMP-2 K$_i$ (nM) | MMP-3 K$_i$ (nM) | MMP-12 K$_i$ (nM) |
|---|---|---|---|---|
| Example 1 | 5800 | 1800 | 750 | 13 |

TABLE 2-continued

| Compound (Example Number) | MMP-1 $K_i$ (nM) | MMP-2 $K_i$ (nM) | MMP-3 $K_i$ (nM) | MMP-12 $K_i$ (nM) |
|---|---|---|---|---|
| 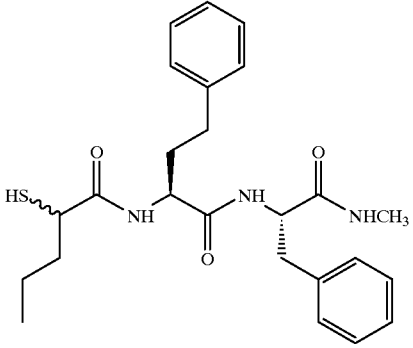<br>Example 6 | 360 | — | 14 | 14 |
| 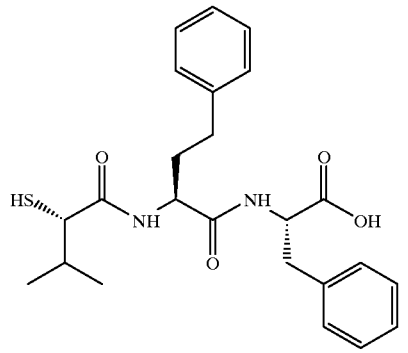<br>Example 2 | 5109 | 731 | 365 | 4 |
| 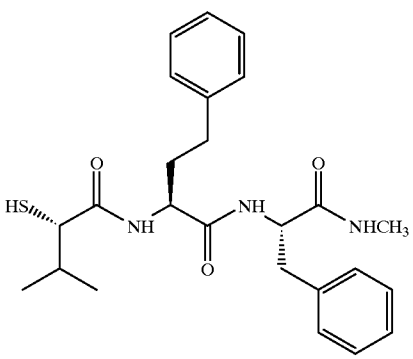<br>Example 7 | 465 | 3.3 | 10 | 0.6 |

The values in Table 2 show that the compounds of the present invention (Examples 1 and 2) are selective for MMP-12 over MMP-1, MMP-2, and MMP-3 compared to their N-methylamide derivatives (Examples 6 and 7).

What is claimed is:

1. A compound of the formula

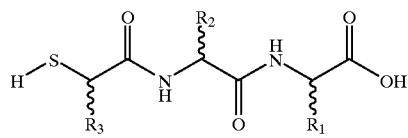

formula (1)

wherein $R_1$, $R_2$ and $R_3$ together are defined as follows:

$R_1$ is hydrogen; and $R_2$ is selected from the group consisting of $C_1$–$C_6$ alkyl, —$(CH_2)_4NH_2$, —$(CH_2)_2$—$S(O)_f$—$CH_3$, and —$(CH_2)_g$—$Ar_{1'}$;

wherein f is 0, 1, or 2;

g is an integer from 1 to 2;

$Ar_{1'}$ is a radical of

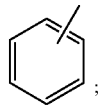

and $R_3$ is selected from the group consisting of $C_1$–$C_4$ alkyl and —$(CH_2)_p$—$Ar_3$, wherein p is an integer from 1–2;

$Ar_3$ is

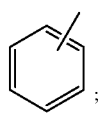

or wherein $R_1$, $R_2$ and $R_3$ together are defined as follows:

$R_1$ is selected from the group consisting of hydrogen, $C_3$–$C_6$ alkyl, and —$(CH2)_d$—$Ar_1$;

wherein d is an integer from 1 to 2;

$Ar_1$ is a radical of

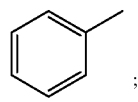

and $R_2$ is selected from the group consisting of —$(CH_2)_4NH_2$ and —$(CH_2)_2$—$S(O)_f$—$CH_3$;

wherein f is 0, 1, or 2; and $R_3$ is selected from the group consisting of $C_1$–$C_4$ alkyl and —$(CH_2)_p$—$Ar_3$, wherein p is an integer from 1–2;

$Ar_3$ is

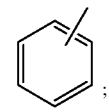

and stereoisomers, pharmaceutically acceptable salts, and hydrates thereof.

2. The compound of claim 1
wherein $R_1$ is hydrogen;

$R_2$ is selected from the group consisting of $C_1$–$C_6$ alkyl, —$(CH_2)_4NH_2$, —$(CH_2)_2$—$S(O)_f$—$CH_3$ and —$(CH_2)_g$—$Ar_{1'}$;

wherein f is 0, 1, or 2;

g is an integer from 1 to 2;

$Ar_{1'}$ is a radical of

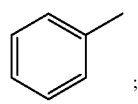

$R_3$ is selected from the group consisting of $C_1$–$C_4$ alkyl and —$(CH_2)_p$—$Ar_3$, wherein p is an integer from 1–2;

53

Ar₃ is

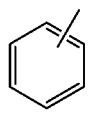

and stereoisomers, pharmaceutically acceptable salts, and hydrates thereof.

3. The compound of claim 1 wherein

R₁ is selected from the group consisting of hydrogen, $C_3-C_6$ alkyl and $—(CH_2)_d—Ar_1$;
  wherein
  d is an integer from 1 to 2;
  Ar₁ is a radical of

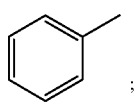

R₂ is selected from the group consisting of $—(CH_2)_4NH_2$ and $—(CH_2)_2—S(O)_f—CH_3$,
  wherein
  f is 0, 1 or 2;
R₃ is selected from the group consisting of $C_1-C_4$ alkyl and $—(CH_2)_p—Ar_3$,
  wherein
  p is an integer from 1–2;
  Ar₃ is

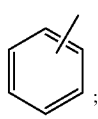

and stereoisomers, pharmaceutically acceptable salts, and hydrates thereof.

4. The compound of claim 3 wherein R₁ is $—(CH_2)_d—Ar_1$.

5. The compound of claim 3 wherein R₁ is $—(CH_2)_d—Ar_1$ wherein d is 1.

6. The compound of claim 3 wherein R₁ is $—(CH_2)_d—Ar_1$ wherein d is 2.

7. The compound of claim 2 wherein R₂ is selected from the group consisting of $C_1-C_6$ alkyl, $—(CH_2)_4NH_2$, $—(CH_2)_2—S—CH_3$, and

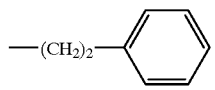

8. The compound of claim 4 wherein R₂ is selected from the group consisting of $—(CH_2)_4NH_2$ and $—(CH_2)_2—S—CH_3$.

9. The compound of claim 5 wherein R₂ is selected from the group consisting of $—(CH_2)_4NH_2$ and $—(CH_2)_2—S—CH_3$.

10. The compound of claim 6 wherein R₂ is selected from the group consisting of $—(CH_2)_4NH_2$ and $—(CH_2)_2—S—CH_3$.

54

11. The compound of claim 1 wherein R₃ is $C_1-C_4$ alkyl.

12. The compound of claim 1 wherein R₃ is 2-propyl.

13. The compound of claim 5 wherein R₃ is $C_1-C_4$ alkyl.

14. The compound of claim 9 wherein R₃ is 2-propyl.

15. The compound of claim 1 wherein the compound is 2-mercapto-pentanoyl-(L)-homo-phenylalanyl-(L)-phenylalanine.

16. The compound of claim 1 wherein the compound is (S)-2-mercapto-3-methylbutyroyl-(L)-homo-phenylalanyl-(L)-phenylalanine.

17. The compound of claim 1 wherein the compound is (S)-2-mercapto-3-methylbutyroyl-(L)-leucyl-(L)-phenylalanine.

18. The compound of claim 1 wherein the compound is (S)-2-mercapto-3-methylbutyroyl-(L)-methionyl-(L)-phenylalanine.

19. The compound of claim 1 wherein the compound is (S)-2-mercapto-3-methylbutyroyl-(L)-lysyl-(L)-phenylalanine.

20. A pharmaceutical composition comprising a compound of claim 1 and a pharmaceutically acceptable carrier.

21. A method of treating smoking-induced emphysema in a patient in need thereof which comprises administering to the patient an effective matrix metalloproteinase inhibiting amount of a compound of the formula

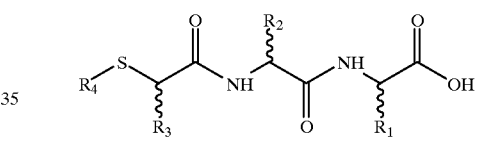

formula (1)

wherein

R₁ is selected from the group consisting of hydrogen, $C_1-C_6$ alkyl, $—(CH_2)_a—CO_2R_5$, $—(CH_2)_a—C(O)NH_2$, $—(CH_2)_4NH_2$, $—(CH_2)_3—NH—C(NH)NH_2$, $—(CH_2)_2—S(O)_b—CH_3$, $—CH_2—OH$, $—CH(OH)CH_3$, $—CH_2—SH$, $—(CH_2)_d—Ar_1$, and $—CH_2—Ar_2$;
  wherein
  a is 1 or 2;
  b is 0, 1, or 2;
  d is an integer from 0 to 4;
  R₅ is selected from the group consisting of hydrogen, $C_1-C_4$ alkyl, and benzyl;
  Ar₁ is a radical selected from the group consisting of

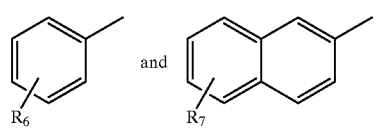

wherein
  R₆ is from 1 to 2 substituents independently selected from the group consisting of hydrogen, halogen, $C_1-C_4$ alkyl, hydroxy, and $C_1-C_4$ alkoxy;
  R₇ is selected from the group consisting of hydrogen, halogen, $C_1-C_4$ alkyl, and $C_1-C_4$ alkoxy;

$Ar_2$ is a radical selected from the group consisting of

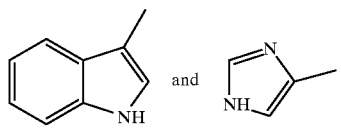

$R_2$ is selected from the group consisting of $C_1$–$C_6$ alkyl, —$(CH_2)_e$—$CO_2R_{5'}$, —$(CH_2)_e$—$C(O)NH_2$, —$(CH_2)_4NH_2$, —$(CH_2)_3$—NH—$C(NH)NH_2$, —$(CH_2)_2$—$S(O)_f$—$CH_3$, —$CH_2$—OH, —$CH(OH)CH_3$, —$CH_2$—SH, —$(CH_2)_g$—$Ar_{1'}$, and —$(CH_2)$—$Ar_{2'}$;
wherein
e is 1 or 2;
f is 0, 1 or 2;
g is an integer from 1 to 4;
$R_{5'}$ is selected from the group consisting of hydrogen, $C_1$–$C_4$ alkyl, and benzyl;
$Ar_{1'}$ is a radical selected from the group consisting of

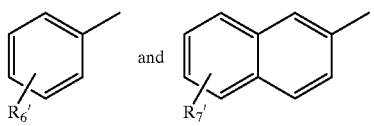

wherein
$R_{6'}$ is from 1 to 2 substituents independently selected from the group consisting of hydrogen, halogen, $C_1$–$C_4$ alkyl, hydroxy, and $C_1$–$C_4$ alkoxy;
$R_{7'}$ is selected from the group consisting of hydrogen, halogen, $C_1$–$C_4$ alkyl, and $C_1$–$C_4$ alkoxy;
$Ar_{2'}$ is a radical selected from the group consisting of

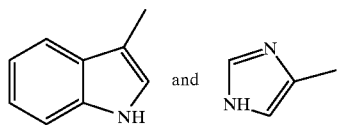

$R_3$ is selected from the group consisting of $C_1$–$C_6$ alkyl, —$(CH_2)_m$—W, —$(CH_2)_p$—$Ar_3$, —$(CH_2)_k$—$CO_2R_9$, —$(CH_2)_m$—$SO_2NR_{8'}$—$Y_1$, and —$(CH_2)_m$—Z—Q
wherein
m is an integer from 2 to 8;
p is an integer from 0–10;
k is an integer from 1 to 9;
W is phthalimido;
$Ar_3$ is selected from the group consisting of

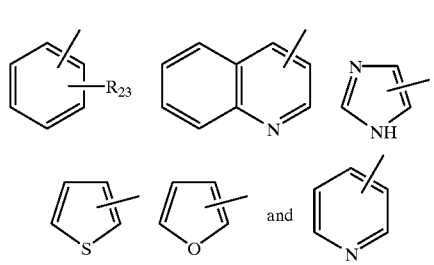

wherein $R_{23}$ is from 1 to 2 substituents independently selected from the group consisting of hydrogen, halogen, $C_1$–$C_4$ alkyl, and $C_1$–$C_4$ alkoxy;
$R_{8'}$ is hydrogen or $C_1$–$C_6$ alkyl;
$R_9$ is hydrogen or $C_1$–$C_6$ alkyl;
$Y_1$ is selected from the group consisting of hydrogen, —$(CH_2)_j$—$Ar_4$, and —$N(R_{24})_2$, or $Y_1$ and $R_{8'}$ are taken together with the nitrogen to which they are attached to form a N-morpholino, N-piperidino, N-pyrrolidino, or N-isoindolyl;
wherein
j is 0 or 1;
$R_{24}$ is hydrogen or $C_1$–$C_6$ alkyl;
$Ar_4$ is

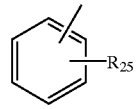

wherein
$R_{25}$ is from 1 to 3 substituents independently selected from the group consisting of hydrogen, halogen, $C_1$–$C_4$ alkyl, and $C_1$–$C_4$ alkoxy;
Z is selected from the group consisting of —O—, —$NR_8$—, —$C(O)NR_8$—, —$NR_8C(O)$—, —$NR_8C(O)NH$—, —$NR_8C(O)O$—, and —$OC(O)NH$—;
wherein
$R_8$ is hydrogen or $C_1$–$C_6$ alkyl;
Q is selected from the group consisting of hydrogen, —$(CH_2)_n$—$Y_2$, and —$(CH_2)_x Y_3$;
wherein
n is an integer from 0 to 4;
$Y_2$ is selected from the group consisting of hydrogen, —$(CH_2)_h$—$Ar_5$ and —$(CH_2)_t$—$C(O)OR_{27}$
wherein
$Ar_5$ is selected from the group consisting of

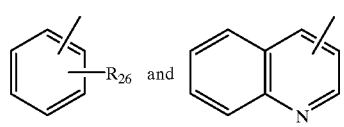

wherein
$R_{26}$ is from 1 to 3 substituents independently selected from the group consisting of hydrogen, halogen, $C_1$–$C_4$ alkyl, and $C_1$–$C_4$ alkoxy;
h is an integer from 0 to 6;
t is an integer from 1 to 6;
$R_{27}$ is hydrogen or $C_1$–$C_6$ alkyl;
x is an integer from 2 to 4;
$Y_3$ is selected from the group consisting of —$N(R_{28})_2$, N-morpholino, N-piperidino, N-pyrrolidino, and N-isoindolyl;
wherein
$R_{28}$ is hydrogen or $C_1$–$C_6$ alkyl;
$R_4$ is selected from the group consisting of hydrogen, —$C(O)R_{10}$, —$C(O)$—$(CH_2)_q$—X and —S—G
wherein
$R_{10}$ is selected from the group consisting of hydrogen, $C_1$–$C_4$ alkyl, phenyl, and benzyl;
q is 0, 1, or 2;

X is selected from the group consisting of

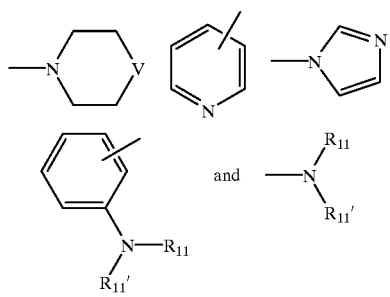

and

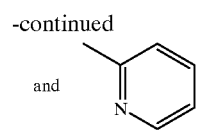

wherein
V is selected from the group consisting of a bond, —CH$_2$—, —O—, —S(O)$_r$—, —NR$_{21}$—, and —NC(O)R$_{22}$—;
wherein
r is 0, 1, or 2;
R$_{21}$ is selected from the group consisting of hydrogen, C$_1$–C$_4$ alkyl, and benzyl;
R$_{22}$ is selected from the group consisting of hydrogen, —CF$_3$, C$_1$–C$_{10}$ alkyl, phenyl, and benzyl;
R$_{11}$ is selected from the group consisting of hydrogen, C$_1$–C$_4$ alkyl, and benzyl;
R$_{11'}$ is selected from the group consisting of hydrogen, C$_1$–C$_4$ alkyl, and benzyl;
G is selected from the group consisting of

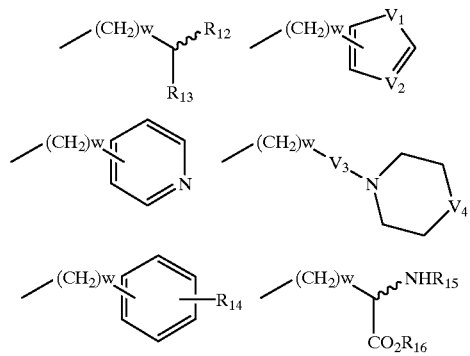

wherein
w is an integer from 1 to 3;
R$_{12}$ is selected from the group consisting of hydrogen, C$_1$–C$_6$ alkyl, —CH$_2$CH$_2$S(O)$_u$CH$_3$, and benzyl; wherein u is 0, 1, or 2;
R$_{13}$ is selected from the group consisting of hydrogen, hydroxy, amino, C$_1$–C$_6$ alkyl, N-methylamino, N,N-dimethylamino, —CO$_2$R$_{17}$, and —OC(O)R$_{18}$;
wherein
R$_{17}$ is hydrogen, —CH$_2$O—C(O)C(CH$_3$)$_3$, C$_1$–C$_4$ alkyl, benzyl, or diphenylmethyl;
R$_{18}$ is hydrogen, C$_1$–C$_6$ alkyl or phenyl;
R$_{14}$ is 1 or 2 substituents independently selected from the group consisting of hydrogen, C$_1$–C$_4$ alkyl, C$_1$–C$_4$ alkoxy, and halogen;
V$_1$ is selected from the group consisting of —O—, —S—, and —NH—;
V$_2$ is selected from the group consisting of —N— and —CH—;
V$_3$ is selected from the group consisting of a bond and —C(O)—;
V$_4$ is selected from the group consisting of —O—, —S—, —NR$_{19}$—, and —NC(O)R$_{20}$;
wherein
R$_{19}$ is hydrogen, C$_1$–C$_4$ alkyl, or benzyl;
R$_{20}$ is hydrogen, —CF$_3$, C$_1$–C$_{10}$ alkyl, or benzyl;
R$_{15}$ is selected from the group consisting of hydrogen, C$_1$–C$_6$ alkyl and benzyl;
R$_{16}$ is selected from the group consisting of hydrogen and C$_1$–C$_4$ alkyl;

and stereoisomers, pharmaceutically acceptable salts, and hydrates thereof.

* * * * *